(12) United States Patent
Cholette et al.

(10) Patent No.: US 8,521,291 B1
(45) Date of Patent: Aug. 27, 2013

(54) DUAL THERAPY ELECTRICAL STIMULATION SYSTEM FOR TREATING METABOLIC AND EATING DISORDERS

(75) Inventors: Martin Cholette, Valencia, CA (US); Ruth Lyons, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 735 days.

(21) Appl. No.: 11/555,166

(22) Filed: Oct. 31, 2006

(51) Int. Cl.
*A61N 1/00* (2006.01)

(52) U.S. Cl.
USPC .................. 607/40; 607/2; 607/115; 607/133

(58) Field of Classification Search
USPC ........................................ 607/2, 115, 133, 40
See application file for complete search history.

(56) References Cited

U.S. PATENT DOCUMENTS

| | | | |
|---|---|---|---|
| 5,263,480 A * | 11/1993 | Wernicke et al. | 607/118 |
| 6,243,607 B1 | 6/2001 | Mintchev et al. | |
| 6,449,511 B1 | 9/2002 | Mintchev et al. | |
| 6,826,428 B1 | 11/2004 | Chen et al. | |
| 2003/0018367 A1 | 1/2003 | DiLorenzo | |
| 2004/0059393 A1 * | 3/2004 | Policker et al. | 607/40 |
| 2004/0147816 A1 | 7/2004 | Policker et al. | |
| 2005/0149141 A1 * | 7/2005 | Starkebaum | 607/40 |
| 2005/0153885 A1 * | 7/2005 | Yun et al. | 514/12 |
| 2005/0245986 A1 * | 11/2005 | Starkebaum | 607/40 |
| 2006/0074450 A1 * | 4/2006 | Boveja et al. | 607/2 |
| 2006/0161217 A1 | 7/2006 | Jaax et al. | |
| 2007/0106337 A1 | 5/2007 | Errico et al. | |
| 2008/0086179 A1 | 4/2008 | Sharma | |
| 2009/0316925 A1 | 12/2009 | Eisenfeld et al. | |
| 2011/0034968 A1 | 2/2011 | Knudson et al. | |
| 2011/0208271 A1 | 8/2011 | Dobak | |

OTHER PUBLICATIONS

NonFinal Office Action, mailed Aug. 30, 2011: Related U.S. Appl. No. 12/196,985.
Chen, J. et al., "Response of the electric activity in the human stomach to water and a solid meal," Med. & Biol. Eng. & Comput. 1991;29:351-367.
Di Bella, L et al., "Behavioral Patterns Proceeding from Liver Thermoreceptors," Physiology & Behavior. 1981;26:53-59.
Mattes, Richard D. Ph.D, RD, "Physiologic responses to sensory stimulation by food: Nutritional implications," J Am Diet Assoc. 1997;97:404-410,413.
Nederkoorn, C. et al., "Cephalic phase responses, craving and food intake in normal subjects," Appetite. 2000;35:45-55.
Nederkoorn, Chantal et al., "Cue reactivity and regulation of food intake," Eating Behaviors. 2002;3:61-72.
Nederkoorn, Chantal et al., "Exposure to binge food in bulimia nervosa: finger pulse amplitude as a potential measure of urge to eat and predictor of food intake," Appetite. 2004;42:125-130.
van de Wall, Esther Henriette Eugenie Marie, "Capsaicin-Sensitive Nerves and Energy Homeostatis: Involvement in satiety and glucose homeostatis," Rijksuniversiteit Groniginen (Mar. 2005).

(Continued)

*Primary Examiner* — Nicole F Lavert

(57) ABSTRACT

An exemplary method for treating an eating or metabolism disorder includes calling for delivery of energy to the stomach using a pulse train that includes use of pulses with a pulse width less than approximately 20 ms, a duty cycle greater than approximately 20% and a pulse train duration of less than approximately 10 seconds and calling for delivery of energy to a vagal nerve. Various other methods, devices, systems, etc., are also disclosed.

16 Claims, 11 Drawing Sheets

(56) References Cited

OTHER PUBLICATIONS

Pederson, J.F., "Sonographic Comparison of Gastric Emptying of Broth and Water: Is There a Promoting Cephalic Factor?" Acta Radiologica. 2005;46:132-134.

Powley, T.L., "Nutritional Implications of Cephalic Phase Responses: Vagal circuitry mediating cephalic-phase responses to food," Appetite. 2000;34:184-188.

Rogers, J. et al., "Cephalic phase of colonic pressure response to food," Gut. 1993;34:537-543.

Sengupta, J.N. et al., "Characteristics of Vagal Esophageal Tension-Sensitive Afferent Fibers in the Opossum," Journal of Neurophysiology. 1989;61(5):1001-1010.

Sobhani, Iradj et al., "Vagal Stimulation Rapidly Increases Leptin Secretion in Human Stomach," Gastroenterology. 2002;122:259-263.

Favretti, Franco MD et al., "Treatment of Morbid Obesity with the Transcend Implantable Gastric Stimulator (IGS): A Prospective Survey," Obesity Surgery. 2004;14(5):666-670.

Diaz Guemes, I et al., "Effect of subthreshold stimulation of vagal nerve on food intake pattern in swine," 9th Annual Conference of the International FES Society, Sep. 2004—Bournemouth, UK.

Konturek, S.J. et al., "Brain-Gut Axis and Its Role in the Control of Food Intake," Journal of Physiology and Pharmacology. 2004;55(1):137-154.

Sobocki, J. et al., "Microchip Vagal Pacing Reduces Food Intake and Body Mass," Hepato-Gastroenterology. 2001;48:1783-1787.

Hinton, Elanor C., et al.; Neural contributions to the motivational control of appetite in humans; European Journal of Neuroscience, vol. 20, pp. 1411-1418, 2004.

Zhang Lei, et al; Thermosensitive transient receptor potential channels in vagal afferent neurons of the mouse; Am J Physiol Gastrointest Liver Physiol 286; G983-G991; 2004.

Krolczyk, G., et al.; Encoding meal in integrated vagal afferent discharge; Journal of Physiology and Pharmacology 2004, 44;1:99-106.

Laskiewicz, J., et al.; Capsaicin induced deafferentiation enhances the effect of electrical vagal nerve stimulation on food intake and body mass; Journal of Physiology and Pharmacology 2004, 55; 1, 155-163.

Forster, J., et al.; Gastric pacing is a new surgical treatment for gastroparesis; The American Journal of Surgery 182 (2001) 676-981.

Travagli, R. Alberto, et al.; Receptors and Transmission in the brain-gut axis: Potential for novel therapies V. fast and slow extrinsic modulation of dorsal vagal complex circuits; Am J. Physiol Gastrointest Liver Physiol 281: G595-G601, 2oo1.

Peles, Shachar, et al.; Enhancement of antral contractions and vagal afferent signaling with synchronized electrical stimulation; Am J Physiol Gastrointest Liver Physiol 285: G577-G585, 2003.

Notice of Allowance, mailed Apr. 5, 2013: Related U.S. Appl. No. 12/196,985.

NonFinal Office Action, mailed Oct. 12, 2012: Related U.S. Appl. No. 12/196,985.

Advisory Action, mailed Apr. 6, 2012: Related U.S. Appl. No. 12/196,985.

Final Office Action, mailed Feb. 1, 2012: Related U.S. Appl. No. 12/196,985.

\* cited by examiner

DUAL THERAPY ELECTRICAL STIMULATION SYSTEM FOR TREATING METABOLIC AND EATING DISORDERS

CROSS-REFERENCE TO RELATED APPLICATIONS

This application is related to copending U.S. patent application Ser. No. 12/196,985, filed Aug. 22, 2008, titled "Detection of Feeding Intent for Use in Treatment of Eating Disorders".

TECHNICAL FIELD

Exemplary methods, devices, systems, etc., presented herein generally relate to implantable electrical stimulation devices for altering food intake.

BACKGROUND

General Information on Food Intake

The human body normally functions in two states: food intake state and a fasting state. The duration and frequency of these states varies from individual to individual. Numerous factors are involved including availability of food as well as psychological and physiological condition.

Regarding food intake, nearly all of the body's energy comes from glucose and fatty acids. After being absorbed in the gastrointestinal tract (GIT), glucose can be taken up by cells and oxidized to generate ATP; linked with other glucose molecules and stored as glycogen; and combined with other glucose molecules and formed into fatty acids. Fatty acids, after being absorbed in the GIT can be oxidized to produce ATP or taken up by cells, combined with glycerol and stored as triglycerides. When a person has a positive energy balance, the hormone insulin plays a primary role in control of metabolic fuel metabolism. The pancreas secretes insulin in response to food intake. Insulin prepares the body for a sudden increase in metabolic fuels by facilitating glucose entry into cells for oxidation or storage. However, insulin inhibits release of fatty acids from fat cells. Absence of insulin (diabetes mellitus) leads to a buildup of blood glucose (hyperglycemia). Common diabetes disorders are type 1 where the body cannot produce insulin and type 2 where the body becomes less responsive to insulin.

Regarding fasting, the body normally relies on conversion of stored metabolic fuels. For example, the body breaks down glycogen and triglycerides to glucose and fatty acids. While the heart is a fatty acid burner, the brain relies on glucose. A group of hormones, sometimes referred to as counterregulatory hormones, mediate the breakdown and mobilization process. These hormones act, in general, counter to the actions of insulin and include epinephrine, glucagon and cortisol/corticosterone.

As discussed herein, various neural circuits control food intake and fasting hormones. Neural processes receive information, communicate information and respond to such information to thereby motivate the individual for food intake or not. While internal information affects such motivated behavior, at times, external information plays a role as well; thus, neural circuits that process internal and external information are involved.

As discussed in more detail below, mechanisms controlling food intake may include brain-based, peripheral-based and periphery to brain-based mechanisms. For example, inhibition of glucose oxidation in the caudal hindbrain increases food intake. Thus, the hindbrain, in contrast to the hypothalamus, contains cells that can monitor glucose availability and control food intake and epinephrine release. Peripheral mechanisms include those associated with the liver. Food passes through the liver where nutrients cause a decrease in food intake. In contrast, providing 2-deoxy-glucose (2DG) to the hepatic portal vein causes an increase in food intake. Information from the liver is conveyed to the brain via, for example, vagal pathways (vagotomy nulls these actions). Thus, a neuronal link exists between periphery and the brain. Perhaps the most complex mechanisms rely on hormones released from the periphery that act on the brain or peripheral organs.

Overall, a need exists for improved therapies to address disorders associated with food intake and metabolism. In particular, such improved therapies should aim to increase responder rate. In other words, a high probability of success should exist for a therapeutic system prior to implantation of the system. Various exemplary devices, methods, systems, etc., described below aim to provide for multiple therapies to address such issues.

SUMMARY

An exemplary method for treating an eating or metabolism disorder includes calling for delivery of energy to the stomach using a pulse train that includes use of pulses with a pulse width less than approximately 20 ms, a duty cycle greater than approximately 20% and a pulse train duration of less than approximately 10 seconds and calling for delivery of energy to a vagal nerve. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Figure 1:
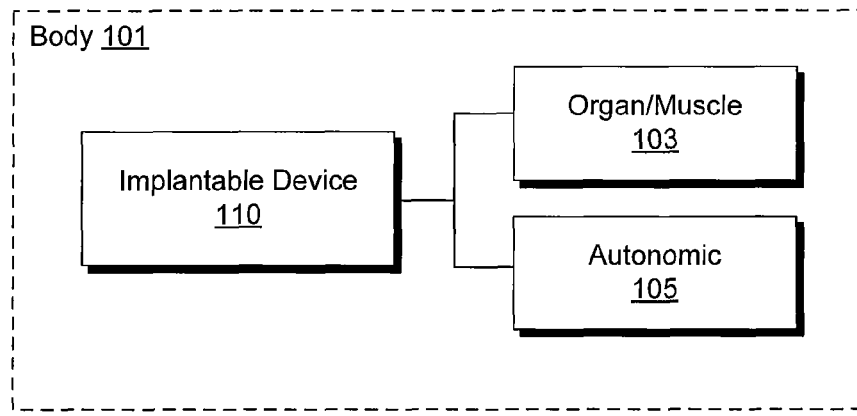
FIG. 1 is a diagram illustrating various exemplary scenarios where an implantable device interacts with organ/muscle and/or autonomic nerves in the body.
Figure 1:
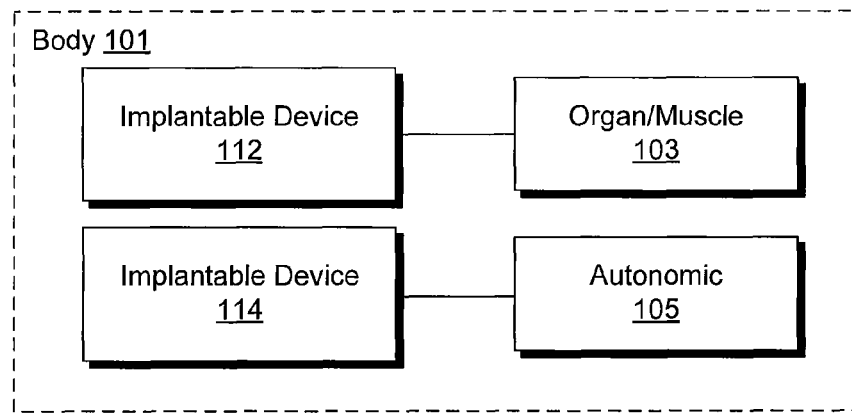
Figure 1:
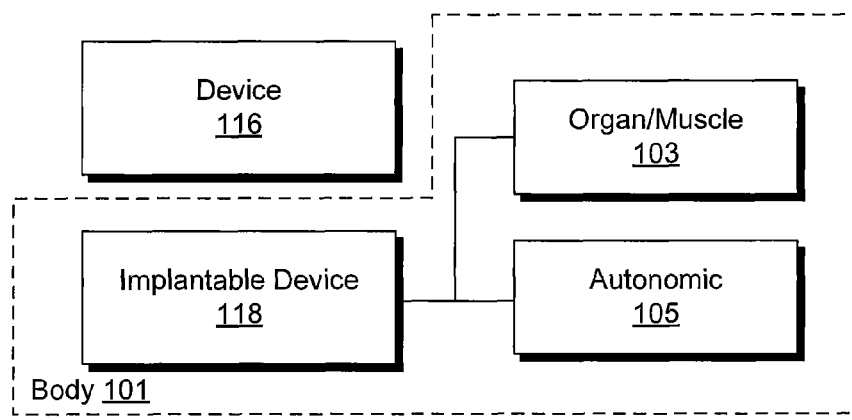

FIG. 1 shows various exemplary scenarios 102, 104 and 106 whereby at least one implantable device (e.g., 110, 112, 114, 118) interacts with an organ and/or muscle of the body 101 and/or interacts with the autonomic nervous system of the body 101. In general, such interactions include interactions that can adjust food intake or provide information relevant to food intake. An exemplary implantable device may optionally provide for cardiac therapy or communicate with a device that can provide for cardiac therapy. An exemplary implantable device may optionally provide for respiratory therapy or communicate with a device that can provide for respiratory therapy.

The exemplary scenario 102 includes a single implantable device 110 that can sense, activate and/or block activity of an organ and/or muscle 103 and/or activity of an autonomic nerve or nerves 105. With respect to food intake, the device 110 may stimulate a vagal afferent pathway and stimulate stomach muscle in a manner that reduces food intake. As described in more detail below, an exemplary method implemented by the device 110 may stimulate the vagal afferent pathway more frequently than the stomach muscle. Such a method may act to conserve power of an implantable device, noting that such a device may be rechargeable or have a replaceable power source. A rechargeable device may rely on an external power source that transmits energy to charge a capacitor or other storage.

The exemplary scenario 104 includes two or more implantable devices 112, 114. In this example, the device 112 senses, activates and/or blocks activity associated with one or more muscles and/or organs 103. The other device 114 senses, activates and/or blocks activity of one or more autonomic nerves 105. In general, the devices 112, 114 operate in a coordinated manner to adjust food intake and/or to provide information relevant to food intake. The devices 112, 114 may include circuits to allow for uni-directional or bi-directional communication. Pseudo-communication may occur via a circuit in one of the devices that detects electrical or other actions of the other device. For example, where the device 112 delivers energy to the stomach, the device 114 may sense the electrical activity via one or more electrodes or other circuits. The device 114 may rely on such information to determine appropriate action (e.g., sensing, activating, blocking, alerting, communicating, etc.).

The exemplary scenario 106 includes an external device 116 and an implantable device 118. The external device 116 may acquire information from the implantable device 118 and/or acquire information about the body 101. For example, the external device 116 may acquire body weight information and then communicate this information to the implantable device 118. In turn, the implantable device 118 may use the communicated information to determine an action related to one or more organs/muscles 103 and/or one or more autonomic nerves 105. In general, the device 118 is capable of delivering therapy aimed at adjusting food intake, for example, reducing food intake, regulating and/or scheduling food intake.

Figure 2:
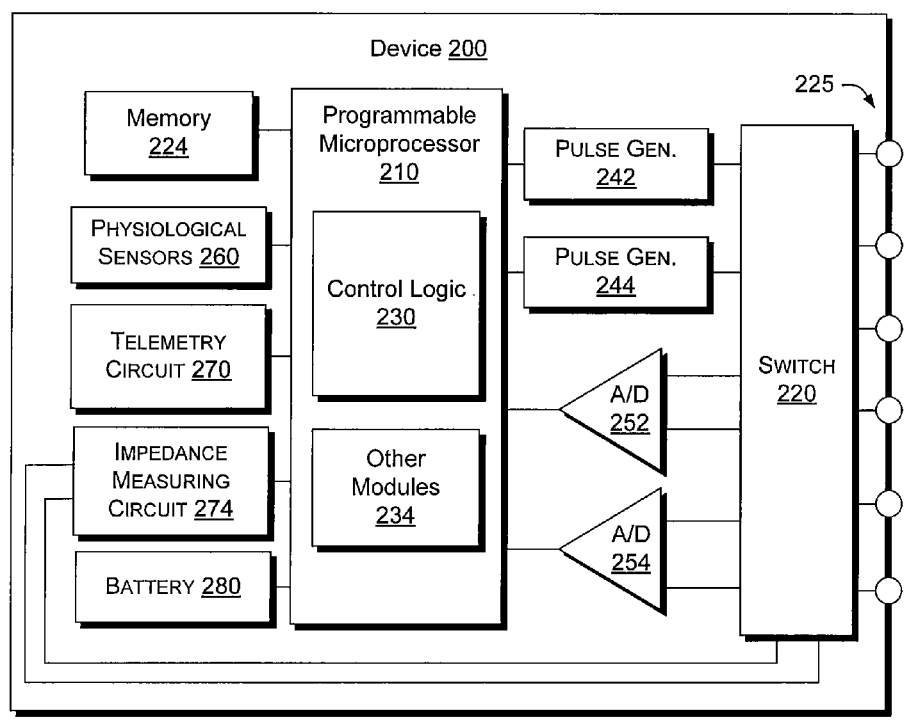
FIG. 2 is a functional block diagram of an exemplary implantable stimulation device illustrating basic elements that are configured to provide one or more therapies related to food intake.

FIG. 2 shows a block diagram of an exemplary device capable of sensing, activating and/or blocking activity of any number of organs, muscles and/or nerves. A basic device may include a processor, memory, one or more inputs, one or more outputs and control logic stored as instructions in the memory and operable in conjunction with the processor. The device 200 includes various additional features.

The exemplary device 200 includes a programmable microprocessor 210 that can implement control logic 230 and other instructional modules 234. Information may be stored in memory 224 and accessed by the programmable microprocessor 210. For delivery activation energy, the device 200 includes one or more pulse generators 242, 244. The pulse generators 242, 244 may rely on a switch 220 for delivery of energy via one or more connectors 225. While a device may include one or more integral leads, in general, a device includes one or more connectors for connecting a lead or leads to the device. More particularly, the connectors 225 provide for electrically connecting one or more electrodes to the circuitry of the device 200. In the example of FIG. 2, the switch 220 may select an appropriate electrode configuration. An electrode configuration may include an electrode from one lead and an electrode from another lead, a case electrode and another electrode or electrodes from a single lead.

The device 200 further includes one or more analog to digital converters 252, 254 for converting analog signals to digital signals or values. The processor 210 may use a signal provided by one of the A/D converters 252, 254 to control a therapy or other process. A control signal from the processor 210 may instruct the switch 220 to select a particular electrode configuration for sensing electrical or other activity. As discussed below, various techniques include sensing nerve activity or other activity.

The device may include one or more physiological sensors 260. Such sensors may be housed within a case of the device 200 (e.g., a motion sensor), include a surface mounted component, include a lead, include a remote sensor, etc. A sensor may provide a digital signal or an analog signal for use by the processor 210 or other circuitry of the device 200. A physiological sensor may provide a signal via one or more of the connectors 225.

For purposes of communication with external or other implantable devices, the device 200 includes a telemetry circuit 270. The telemetry circuit 270 may include one or more antennae for transmission and/or receipt of electromagnetic signals. Such a circuit may operate according to a specialized frequency or frequencies designated for medical devices. Various conventional implantable devices rely on an associated programmer, which is an typically an external computing device with a communication circuit suitable for communicating with an implantable device for purposes of data transfer, status checks, software download, etc. Where the circuit 270 communicates with an implantable device or a device in electrical connection with a patient's body, then the body may be a conductive medium for transfer of information. For example, the circuit 270 may be capable of communication with a specialized wristwatch where the body is relied upon as a conductor.

The device 200 further includes an impedance measuring circuit 274. Such a circuit may rely on instructions from the processor 210. For example, the processor 210 may instruct the circuit 274 to provide a measured impedance for a particular electrode configuration. In such an example, the processor 210 may also instruct the switch 220 to provide the circuit 274 with a particular electrode configuration. Impedance information may be used by the processor 210 for any of a variety of purposes. The processor 210 may store impedance or other information to memory 224 for later use or for transmission via the telemetry circuit 270.

The device 200 includes a power source, which is shown as a batter 280 in the example of FIG. 2. The battery 280 powers the processor 210 and optionally other circuitry, as appropriate. In general, the battery 280 provides power to the pulse generators 242, 244. Consequently, the battery 280 provides for operation of circuitry for processing control logic, etc., and provides for energy to activate tissue. A lead-based sensor may connect to the device 200 via one or more of the connectors 225 and be powered by the battery 280. The battery 280 may be rechargeable, replaceable, etc.

While the device 200 includes particular features, various exemplary devices, systems, methods, etc., may use or be implemented using a different device with more or less features.

Figure 3:
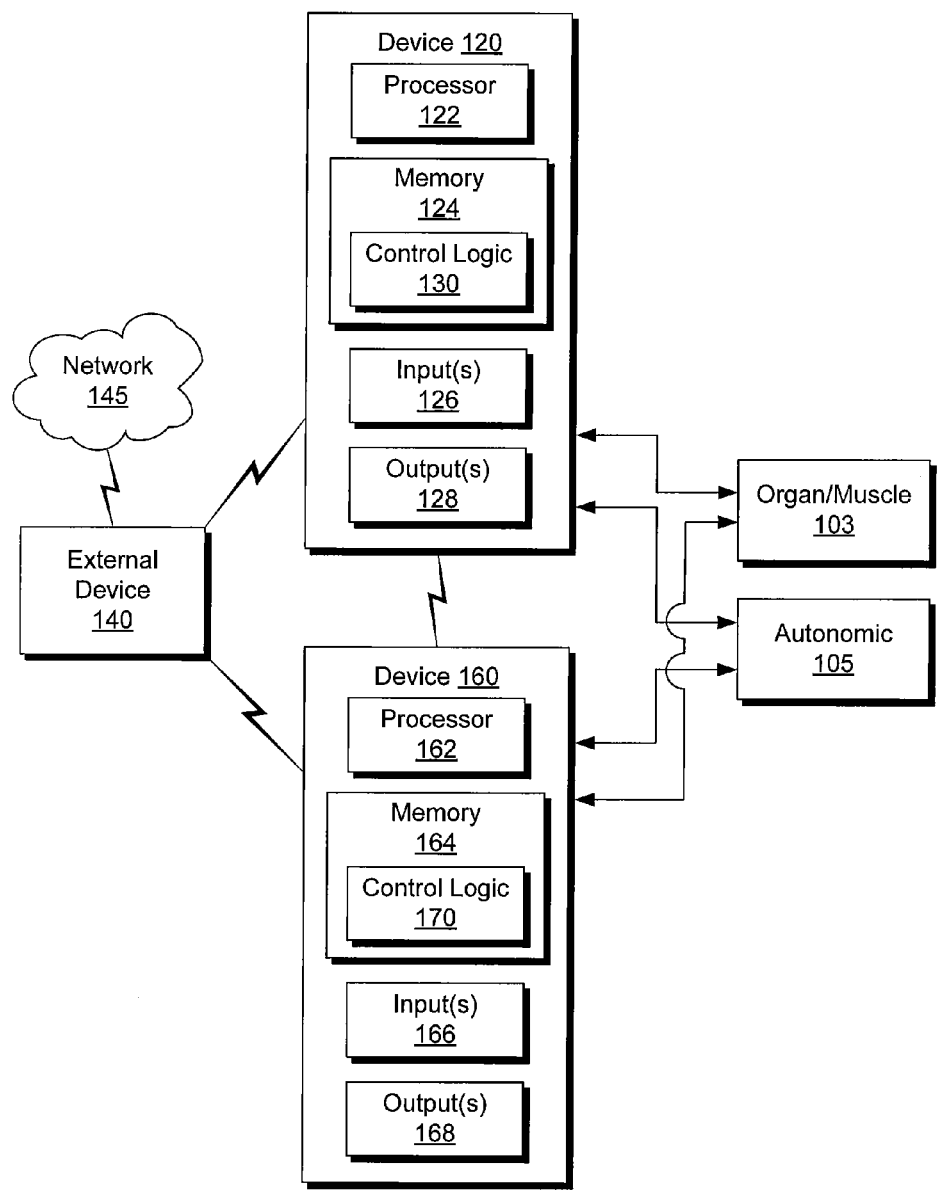
FIG. 3 is a block diagram of an exemplary arrangement of devices for delivering one or more therapies related to food intake.

FIG. 3 shows an exemplary arrangement 300 that includes two implantable devices 120, 160. The implantable device 120 includes a processor 122, memory 124, one or more inputs 126, one or more outputs 128 and control logic 130 stored as instructions in the memory 124 and operable in conjunction with the processor 122. The implantable device 160 includes a processor 162, memory 164, one or more inputs 166, one or more outputs 168 and control logic 170 stored as instructions in the memory 164 and operable in conjunction with the processor 162. The devices 120, 160 may include uni-directional and/or bi-directional communication circuits.

An external device 140 includes one or more circuits to allow for uni-directional and/or bi-directional communication with at least one of the implantable devices 120, 160. The external device 140 is optionally in communication with a network 145 (e.g., intranet, Internet, etc.). The external device is optionally a device programmer.

The implantable devices 120, 160 can sense, activate and/or block activity associated with one or more organs and/or muscles 103 and/or activity associated with one or more autonomic nerves 105. For example, the device 120 may be a cardiac therapy device that can delivery cardiac pacing therapy and optionally autonomic nerve stimulation while the device 160 may be an obesity therapy device that can delivery stomach muscle stimulation and optionally autonomic nerve therapy. Coordinated operation of the two devices 120, 160 may occur via the external device 140 and/or via communication between the devices 120, 160 (uni-directional and/or bi-directional). In general, at least one of the implantable devices 120, 160 pertains to a therapy that aims to adjust food intake.

With respect to food intake therapies, the mechanisms are fairly complex and not all mechanisms are understood. As discussed below, evidence exists to support the existence of some mechanisms. However, an exemplary implantable device or devices may include learning algorithms whereby mechanisms are uncovered, utilized or otherwise better understood through use of various parameters for activation and/or blocking and/or through sensing activity associated with food intake or lack thereof and/or as a consequence of activating and/or blocking.

Figure 4:
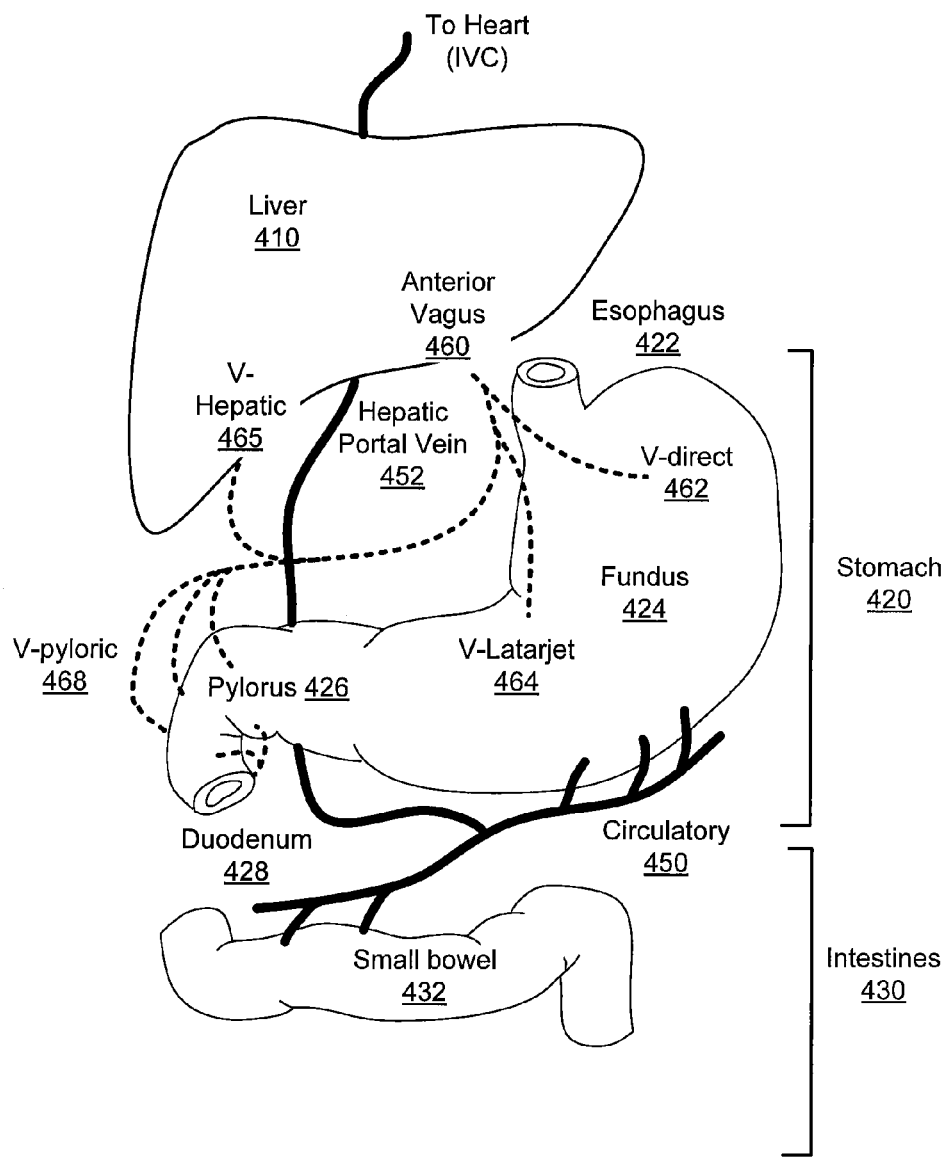
FIG. 4 is an approximate anatomical diagram of various organs and pathways.
Figure 5:
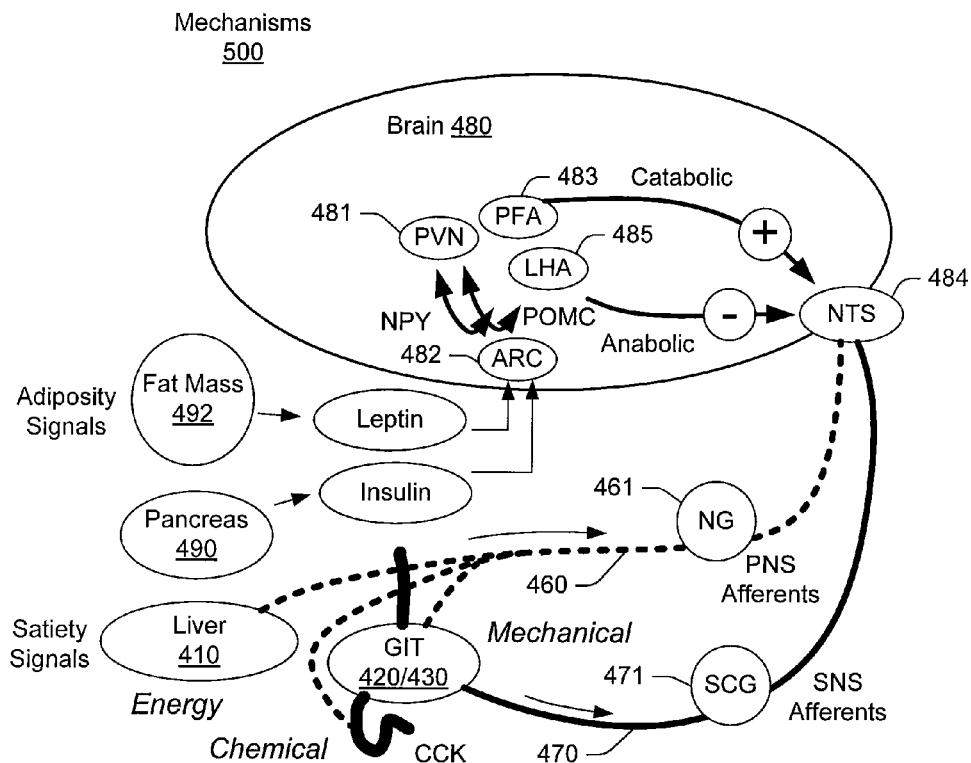
FIG. 5 is a diagram of various mechanisms and pathways associated with food intake.

FIG. 4 is an anatomical diagram 400 of various subthroacic organs, nerves and circulatory routes. FIG. 5 is a diagram 500 that shows various neural circuits related to organs and the brain. The discussion that follows refers to the diagrams 400 and 500 of FIGS. 4 and 5, respectfully. The exemplary devices of FIGS. 1, 2 and 3 optionally sense activity of and/or activate various mechanisms discussed below. Exemplary methods follow that pertain to some non-exhaustive examples.

General Nervous System

Various studies refer to a "brain-gut axis" as a primary mechanism for control of food intake. A review by Konturek et al., "Brain-gut Axis and Its Role in the Control of Food Intake", *J Physiol. Pharma.* 2004, 55, 1, 137-154, recognizes that the gastrointestinal tract (GIT) interacts with the central nervous system (CNS) and the enteric nervous system (ENS) where the CNS and ENS form the brain-gut axis.

The ENS includes specific innervations and plexuses associated with the GIT. For example, the GIT includes a myenteric plexus known as the Auerbach plexus and a submucous plexus known as the Meissner plexus. These plexuses are primarily associated with parasympathetic aspects of the autonomic nervous system. The Auerbach plexus is located between the longitudinal and circular layers of muscle in the tunica muscularis (generally from pylorus to duodenum) and relates to tonic and rhythmic contractions. The Meissner plexus is buried in the submucosa and relates to epithelial cell function and GIT blood flow. Another plexus, the coeliac plexus, is associated primarily with sympathetic aspects of the autonomic nervous system.

As already inferred, interactions exist between these ENS plexuses and the autonomic nervous system, in particular, a vagal pathway and a splanchnic path exist between the CNS and the ENS. The parasympathetic vagal pathway includes cholingeric nerves (about 80% to 90% unmyelinated C-fibers) while the sympathetic splanchnic pathway includes noradrenergic nerves. Regarding interactions, consider that the Valsalva maneuver, commonly associated with parasympathetic activation, as well as increasing intraabdominal pressure (e.g., squat position) can increase normal defectation.

With respect to more specific routes of autonomic innervation, more generally, vaso-vagal reflexes include sensory vagal afferents, second-order integrative neurons of the nucleus of the solitary tract (NTS) and efferent vagal neurons of the dorsal or posterior motor nucleus (DMN). Various studies indicate that the left vagus supplies efferent preganglionic fibers mainly to the anterior surface of the stomach (also known as the anterior vagus) and that the right vagus supplies efferent preganglionic fibers mainly to the posterior surface of the stomach (also known as the posterior vagus). For example, the diagram 400 of FIG. 4 shows the anterior vagus 460 as it tracks from the esophagus 422 to the liver 410, the stomach 420 and the intestines 430. In addition both vagi send branches to the coeliac plexus; however, the degree of interaction with the primarily sympathetic coeliac plexus is suggested to be minimal. The parasympathetic preganglionic vagal fibers penetrate the layers of the gastric wall, to form synapses in the ganglion cells of the Auerbach plexus and in the Meissner plexus. Postganglionic fibers emerge from the plexuses and supply musculature and mucosa.

The coeliac plexus, also known as the solar plexus, is a junction for autonomic nerves supplying the upper abdominal organs (liver, gall bladder, spleen, stomach, pancreas, kidneys, small bowel, and about two-thirds of the large bowel). The coeliac plexus receives sympathetic nerves from the greater splanchnic nerve (around T5/6 to T9/10 vertebrae), the lesser splanchnic nerve (around T10/11 vertebrae) and the least splanchnic nerve (around T11/12 vertebrae). As already mentioned, the upper abdominal organs receive their parasympathetic supply from the left and right vagal trunks which pass through the coeliac plexus without any known significant interaction.

Brain-Gut Axis

The brain-gut axis also relies on afferent signals from the GIT and other organs. Afferent signals from the upper GIT are transmitted by the vagi, splanchnic mesenteric nerves, and pelvic afferents. Together, these afferent nerves provide the peripheral extrinsic neural part of the gut-brain axis. The upper GIT is largely innervated by vagal afferents; the pelvic afferents are limited to the lower or large bowel, while splanchnic afferents innervate much of the GIT. The intrinsic, enteric neural systems such as the myenteric and submucosal plexuses (Auerbach and Meissner) may mediate between GIT mucosal and muscular events and extrinsic neural signaling.

The vagus nerve consists of both sensory and motor axons. In the periphery, as already mentioned, the vagus enters the abdomen with two trunks (the right, dorsal or posterior and the left, ventral or anterior) that track generally along the esophagus. When the vagi cross the diaphragm, in most individuals they divide into five distinctive branches: (i-ii) paired gastric branches, (iii-iv) paired celiac branches and (v) a single hepatic branch that originates from the ventral trunk.

The diagram 400 of FIG. 4 shows various gastric branches of the anterior vagus 460. In particular, the diagram 400 includes direct branches 462 to the fundus 424 (V-direct), pyloric branches 468 to the pylorus 426 (branches emanating from vagal supply to liver 410 that include superior pyloric nerves and inferior pyloric nerves), a hepatic branch or branches 465 (V-hepatic) and the anterior nerve of Latarjet 464 (V-Latarjet, principal anterior nerve of lesser curvature of the fundus 424). Again various branches are linked to the aforementioned Auerbach plexus and Meissner plexus.

The diagram 500 of FIG. 5 shows a more general representation of the anterior vagus 460 as it tracks to the brain 480. As already mentioned, the vagus includes primarily C-fibers. Ingestive and visceral reflexes are mediated by nociceptive or chemosensitive C-fibers which have their cell bodies in the nodose ganglia 461 and show a viscerotopic distribution in the nucleus of the solitary tract 484 (NTS) of the brain 480.

Evidence based on anterograde tracing after injections into the individual subdiaphragmatic vagal branches show discrete, yet somewhat overlapping, NTS 484 termination fields for each vagal branch. Thus, the NTS 484 contains viscerotopic and at least some information specific to a particular vagus branch. As already discussed, the hepatic branch 465 of the anterior vagus 460 includes branches that supply other regions. While pyloric branches 468 and fundus branches 462, 464 are shown in the diagram 400 of FIG. 4, other branches also exist (e.g., antrum, duodenum, and caecum), which is consistent with the general notion that individual gut vagal branches innervate multiple GIT segments. Thus, as with the aforementioned efferent innervation of the GIT, a gastrointestinal target can be innervated by vagal afferents from more than one gut vagal branch.

While various exemplary techniques discussed herein focus on afferent nerves, such techniques optionally sense, activate or block efferent nerve activity. As already mentioned, various efferent nerves project from the DMN, a structure just anterior of the NTS 484. The DMN contains numerous dendrites penetrating the NTS and the Area Postrema (AP). About 95% of preganglionic neurons in the DMN contribute to projections to the stomach suggesting that the efferent part of the vagus nerve is highly involved in the motor innervation of the stomach.

Again, as already mentioned, the posterior vagus appears to have more efferent character while the anterior vagus appears to have more afferent character with respect to the GIT. Hence, as in the afferent projections, each vagal branch contains the axons of a topographically distinct column of cells within the DMN. Therefore, the afferent-efferent viscerotopic and branch specific organization of the vagus likely reflects distinct neurophysiological reflexes and functions involved in ingestion. Such an organization may be used to further the goals of various exemplary techniques discussed herein.

Vagal afferents appear to be sensitive to a variety of stimuli. Different populations of vagal afferents with terminations in the GIT indicate different sensory modalities, for example, reaction to mechanical as well as chemical stimulation. More specifically, vagal endings in the longitudinal and circular muscle layers are also defined as intramuscular arrays (IMAs) and have been suggested to be in-series tension receptors (e.g., mechanical sensors).

Vagal afferents in the myenteric plexus (Auerbach) throughout the GIT are called intraganglionic laminar endings (IGLEs) and exhibit characteristics of a tension receptor. Thus, evidence indicates that vagal afferent fibers play a role in volume detection of the stomach and gut, which may contribute to the process of satiation. This role is supported by neurophysiological studies that link the vagus to the process of satiation and meal termination. Various exemplary techniques discussed herein optionally include sensing, activating and/or blocking vagal afferent fibers associated with the myenteric plexus (Auerbach) to thereby affect food intake of an individual.

As can be appreciated, a variety of chemical messengers exist that play a role in food intake. The diagram 500 of FIG. 5 shows various structures and refers to some messengers. Such messengers include ghrelin (from stomach 420), leptin (from fat mass 492), insulin (from pancreas 490), cholecystokinin (from small intestine 430), peptide YY (from intestines 430), melanotropin (from arcuate nucleus 482), agouti-related peptide (from arcuate nucleus 482), neuropeptide Y (from arcuate nucleus 482). Some details are discussed below for some of these chemical messengers.

Ghrelin

Ghrelin is an endogenous ligand for the growth hormone secretagogue receptor (GHS-R) located in the anterior pituitary and it is the only identified gut hormone (produced in the stomach 420) that stimulates appetite and food intake. Plasma ghrelin concentrations rise immediately before food intake and fall postprandially. Intravenous ghrelin suppresses vagal afferent signaling while vagal efferent signaling participates in the starvation-induced rise in ghrelin. This effect is abolished by vagotomy in rats without affecting the usual postprandial decline in baseline plasma ghrelin concentrations, suggesting separate pathways. Various exemplary methods disclosed herein optionally include sensing, activating and/or blocking of vagal afferent nerves and/or vagal efferent nerves to thereby affect food intake.

Circulating ghrelin is also involved in central appetite regulation and energy balance. Intracerebroventricular (ICV) ghrelin stimulates neuropeptide Y (NPY) and agouti related protein (AgRP) neurons in the hypothalamus and ICV administration of ghrelin in rats decreases latency after the first meal and results in hyperphagia from increased meal frequency rather than meal size. These findings suggest that circulating ghrelin functions to initiate meals.

Fasting plasma ghrelin is significantly lower in obese subjects and negatively correlates with body mass index, percent body fat, fasting insulin and leptin (possibly a physiological adaptation to the long-term positive energy balance associated with obesity). During dieting, increases in ghrelin concentration correlate with the extent of weight loss. Ghrelin may contribute to the difficulty in maintaining diet-induced weight loss because obese patients lack the normal postprandial decline in plasma ghrelin level.

A proposed obesity therapy uses rimonabant, a CB1 receptor antagonist, which has been shown to decrease plasma ghrelin in fed rats and suppress the preprandial rise in ghrelin in fasting rats. Various exemplary techniques disclosed herein optionally include drug therapy whereby administration of a drug such as, but not limited to, rimonabant.

Another potential obesity drug is MK-677, a synthetic ligand for GHS-R that has been shown to impair oral glucose tolerance when administered orally to obese males. Altered ghrelin levels after RYGB may contribute the reversal of insulin resistance through an effect at GHS-R. Further studies are needed to determine whether MK-677 has feeding-altering ability similar to that of ghrelin.

Leptin

Leptin (Greek leptos, meaning thin) is produced by white adipose tissue (e.g., fat mass 492) and conveys information to the hypothalamus and hindbrain as to energy stored in fat. Leptin acts to suppress appetite, affect energy expenditure and regulate euroendocrine function and metabolism.

Low-dose leptin in humans reverses the thyroid hormone suppression associated with maintaining a 10% weight loss, which demonstrates that secretion of thyroid hormones may be related to plasma leptin concentrations during periods of weight loss and maintenance.

Leptin inhibits the stress-responsive secretion of the hypothalamus-produced corticotropin releasing hormone (CRH) in mice and is postulated to lead to CRH receptor up-regulation, a finding that correlates with the enhanced secretion of ACTH (the hormone that triggers cortisol secretion from the adrenal glands) by the pituitary gland, which is a response associated with insulin resistance in obese subjects given CRH.

Obese people have elevated circulating leptin levels where the more obese, the higher the level. Leptin resistance is thought to play a role in obesity. Low levels of circulating leptin may provide a signal that acts to prevent starvation. Again, the human body has more mechanisms to prevent starvation than to prevent obesity.

Insulin

The beta cells of the Islets of Langerhans of the pancreas 490 produce insulin. Circulating insulin levels increase upon food intake and are proportional to body fat. Insulin promotes transport of glucose from the circulatory system into tissues, stimulates uptake of glucose and deposition of glycogen in the liver 410, decreases release of glucose by the liver 410, decreases food intake and increases energy expenditure via action on the hypothalamus and/or hindbrain.

Cholecystokinin

Cholecystokinin (CCK) acts as a satiety hormone and is produced by a population of I cells (mucosal endocrine cells) in the small intestine 432 by presence of nutrients in the duodenum. Evidence indicates that CCK and the vagal action are intimately linked. CCK is known to induce satiety after peripheral administration whereby vagal afferents 460 are required for the effects of CCK on food intake (ablation of these vagal afferents 460 by systemic capsaicin treatment abolishes the action of CCK). CCK receptors to induce satiation exist on vagal afferents 460 and in the nodose ganglion 461. Various exemplary techniques discussed herein optionally include sensing, activating and/or blocking vagal afferents 460 as they relate to absence or presence of CCK to thereby affect food intake.

Evidence gained through administration or examination of CCK suggests that vagal afferents 460 are involved in the long-term regulation of energy homeostasis. For example, when rats maintained on a high fat diet are exposed to increased levels of endogenous CCK, they show a reduced sensitivity to exogenous CCK.

Various studies indicate that stimuli related to food intake (such as mechanical distension, chemical composition of luminal contents, gut peptides and neurotransmitters) can be sensed by vagal afferents 460 and thereby play a role in satiation and meal termination. Vagal afferents 460, receptive to CCK, may play an indirect role in the long-term regulation of energy balance. Various exemplary techniques disclosed herein optionally sense, activate and/or block vagal afferent activity to thereby affect long-term regulation of energy balance.

With respect to mechanical effects, pyloric cuff experiments and sham feeding preparations support the proposition that the stomach 420 detects volume. Hungry animals eat significantly longer and more when the food is drained from the stomach 420. Likewise, when rats eat a very large meal or receive gastric preloads with occlusion of the pyloric cuff rats eat less than with the cuff open. In addition, a study showed that saline was as effective as a liquid diet to induce satiation when gastric emptying was prevented by pyloric cuffs, which indicates that the stomach 420 is primarily involved in volume detection. Such a finding is confirmed by the observation in humans that reduction of stomach capacity by banding is often used to treat severe obesity.

With respect to digestion processes, most absorption and enzymatic activity occurs in the small intestine 432. Humoral factors involved in the process of satiation are also secreted by the small intestine 432 (e.g., CCK); hence, the small intestine 432 is thought to be primarily involved in nutrient sensing. Some vagal afferents 460 respond to infusions of specific nutrients as carbohydrate, fatty acids or amino acids. Thus, vagal afferents 460 innervating the small intestine 432 are able to respond to different nutrients. There are indications that specific nutrients may be sensed by anatomically distinct populations of visceral afferent neurons 460.

In a normal meal, gastric stimulation occurs simultaneously with intestinal stimulation. Therefore, it is likely that these responses are modulated by humoral factors of the duodenum (e.g. CCK) and the stomach 420 (e.g. leptin and grehlin).

Other Factors

Other chemical messengers include neuropeptide Y (increase food intake), AgRP (increase food intake and a-MSH antagonist) and a-MSH (inhibit food intake).

PYY is one of a family of peptides, including NPY and pancreatic polypeptide (PP), a hormone secreted postprandially from the PP cells of the islets of Langerhans of the pancreas 490. The endogenous forms of PYY (PYY1-36 and PYY3-36) are synthesized by the GIT 420/430 and released into the circulation after a meal. PYY3-36 infusion in obese and lean subjects induces a similar inhibition of appetite and food intake, resulting in reduced cumulative 24-hour food intake.

Serotonin is an important ENS neurotransmitter and paracrine hormone. Some 95% of the body's serotonin is expressed in the GIT 420/430, most of which is released by its entrochromaffin epithelial cells in response to luminal pressure (intrinsic peristaltic reflex), vagal stimulation, nociception (nociceptive reflex), and other chemical signals. Autonomic nervous system efferents modulate ENS-initiated changes in gut motility, altering nutrient absorption based on small bowel transit time.

Brain Structures

With respect to the role of the brain 480, many have focused on the arcuate nucleus of the hypothalamus 482

(ARC) and the paraventricular nucleus of the hypothalamus 481 (PVN). Many have hypothesized that circulating ghrelin, leptin and insulin act in the ARC 482 to signal the status of body energy available. Arcuate neurons producing a-MSH or NPY/AgRP project to neurons in the vicinity of the PVN 481 and, in response, food intake and energy expenditure are adjusted. However, details of specific mechanisms remain unknown. The role of insulin has been doubted as playing being major, the role of leptin is unresolved, lesions on ARC 482 have little effect on energy balance and NPY or AgRP gene knock-out have little effect either. Some have begun to focus more on the hindbrain. In any instance, mechanisms appear to be complex and to some extent redundancies exist. The existence of redundancies indicates that a desired result may be achieved in one or more manners.

While mechanisms remain to be detailed, it is without a doubt that various mechanisms allow for communication of information from the GIT 420/430 to the brain 480. Nutrients stimulate chemoreceptors in the GIT 420/430, pancreas 490, and liver 410, whereas bowel distention stimulates vagal afferents 460 and mechanoreceptors. Glucose-sensitive cells exist within the NTS 484 and ARC 482.

As already mentioned, chemical and pressure changes in the GIT 420/430 are transmitted via vagal afferents 460 to the NTS 484. Evidence indicates that nutrients simultaneously stimulate enteroendocrine cells to secrete appetite regulatory hormones, including CCK from I cells in the duodenum and jejunum, PYY and glucagon-like peptide-1 (GLP-1) from L cells primarily in the ileum and colon, glucose-dependent insulinotropic polypeptide (GIP) from K cells in the duodenum, and ghrelin from oxyntic cells (X/A-like cells in rodents and P/D1 cells in humans) primarily in the fundus 424.

CCK secreted during meals acts as a paracrine hormone at CCK1 receptors on mechanosensitive vagal afferents 460 located primarily in the pyloric sphincter and proximal duodenum (e.g., V-pyloric 468). CCK is thought to induce short-term satiety by sensitizing vagal mechanoreceptors to gastric and duodenal distention. CCK is also thought to decrease meal size by inhibiting gastric emptying, thereby augmenting the nutrient preload sensed by vagal afferents 460 and the NTS 484. NTS 484 pro-opiomelanocortin (POMC) neurons are activated by intraperitoneal injections of CCK in mice, and melanocortin 4 receptor (MC4R) expression is required for CCK-induced suppression of food intake.

The thyroid also plays a role in metabolism. Thyroid hormones enhance the effects of norepinephrine, increasing basal metabolic rate, thermogenesis, and lipolysis. Low-dose leptin in humans reverses the thyroid hormone suppression associated with maintaining a 10% weight loss, which demonstrates that secretion of thyroid hormones may be related to plasma leptin concentrations during periods of weight loss and maintenance.

The sympathetic nervous system also plays a significant role in the regulation of energy balance, and there is evidence of its dysfunction in obese persons. Analysis of heart rate variability in obese subjects suggests an increase in basal sympathetic activity and sympathetic response to cold exposure is blunted in obese subjects. Referring to the diagram 500 of FIG. 5, a sympathetic, splanchnic pathway 470 connect to the brain 480 via a superior cervical ganglion 471. The sympathetic pathway 470 can provide afferent information to the NTS 484. The diagram 500 also shows the periformical area (PFA) 483 and lateral hypothalamus area (LHA) 485 as playing a role in metabolic mechanisms.

Vaso-Vagal Reflexes

The aforementioned term "gut-brain axis" refers to the observation that most visceral primary afferents have their nerve endings in the DMN. The process of satiation appears to be controlled by a reflex mechanism known as vago-vagal reflexes, noting that forebrain structures are not required for the inhibition of food intake (decerebrated rats still show satiation to food and injection of CCK). In other words, visceral feedback from the GIT tract to brainstem areas is sufficient to induce satiation. More broadly, vaso-vagal reflex circuits in the medulla are responsible for the smooth coordination of the digestive processes carried out from the oral cavity to the transverse colon.

A study by Travagli et al., "Receptors and Transmission in the Brain-Gut Axis: Potential for Novel Therapies: V. Fast and slow extrinsic modulation of dorsal vagal complex circuits", *Am J Physiol Gastrointest Liver Physiol* 281: G595-G601, 2001, focused on extrinsic modulation of these vago-vagal reflex circuits, with a particular emphasis on modulation by "fast" classic neurotransmitters and by "slow" neuromodulators.

A dissertation by van de Wall, "Capsaicin-sensitive nerves and energy homeostatis: Involvement in satiety and glucose homeostasis", Rijksuniversiteit Groniginen (March 2005), details various vagal afferent pathways and mechanisms.

While various GIT hormones can effect significant changes in GIT function by acting on vagal afferents, studies suggest that GIT hormones can also exert control over digestion by acting directly on neurons of the dorsal vagal complex, for example, to control vagal efferent outflow to the viscera. Further, chemical messengers produced by the immune system can also affect function of neurons of the gastric vago-vagal reflex control circuit.

Electrical Stimulation of Vagal Pathways

With various relationships between vagal pathways and food intake having been established or inferred, some researchers have studied electrical stimulation of these pathways. For example, a study by Sobocki et al., "Microchip vagal pacing reduces food intake and body mass", *Hepatogastroenterology* 48: 1783-1787, 2001, relied on use of microchips to stimulate the vagal afferents in a rabbit model whereby the results suggested that reduced activity of vagal afferent fibers could be involved in weight gain.

Another study, applied the findings of Sobocki et al., to a swine model (Diaz Guemes et al., "Effect of subthreshold stimulation of vagal nerve on food intake pattern in swine", *9th Annual Conference of the International FES Society* September 2004, Bournemouth, UK). This study pointed to the bigger size of the porcine ventral vagal trunk and noted that the electrical impulses applied to the vagal nerve for the both studies were constant in voltage. The researchers stated that because the intensity of the impulses varies according to the nerve diameter (according to Ohms Law) in both species, different fibers may perform different functions when being stimulated in each species using the same stimulation parameters (also noting that stimulation subthreshold may be lower in fast conducting fibers than in slow ones).

While certain vagal nerve stimulation parameters provoked a decrease in body weight and food intake in rabbits, these proved to be subthreshold for changing food intake pattern in pigs, yet, increased systemic gastrin and insulin. Sobocki et al. noted that such findings have been reported by others, referring to a study that applied vagal stimulation with parameters of 13.5 mA, 10 Hz, 5 msec, 10 min to stimulate insulin secretion in dogs and two other studies whereby vagal stimulation increased gastrin concentration. The study of Sobocki et al. concluded that vagal nerve stimulation using parameters that reduced food intake in rabbits was not enough to provoke changes in short term ingestive behavior in swine, but stimulated insulin and gastrin secretion.

Other studies have used electrical vagal nerve stimulation to better understand mechanisms of food intake. For example, a study by Laskiewicz et al., "Capsaicin induced deafferentation enhances the effect of electrical vagal nerve stimulation on food intake and body mass", *J Physiol Pharmacol* 55: 155-163, 2004, examined the effects of neuromodulation of the vagus using an implanted microchip. The study noted that such electrical stimulation reduced fasting glucose levels and that this effect was enhanced when combined with capsaicin treatment, which supports a role for the vagus in glucose homeostasis.

Another study (Forster et al., "Gastric pacing is a new surgical treatment for gastroparesis", *Am J Surg* 2001; 182 (6): 676-681) stimulated the antral part of the stomach with a low energy signal and achieved a decrease in the severity and frequency of nausea and vomiting. This result demonstrates that afferent vagal information could be modulated not only by vagal stimulation but also by gastric stimulation.

Stimulation may occur, and be effective, at one or more sites. For example, direct stimulation of the antral part of the stomach may be used to introduce antiperistaltic gastric waves to decrease food intake or stimulation of ventral vagus may be used to reduce food intake. As already mentioned, different stimulation parameters and nerve size (e.g., diameter) can play a role in the end result caused by electrical stimulation. Stimulation of the stomach to cause contraction of the stomach is discussed in detail further below with reference to FIG. 6.

As already mentioned, vagal afferents 460 conduct signals form the stomach 420 to the NTS 484 carrying information about the size and chemical composition of a meal, which is transmitted by other specific connections to satiety connections in the brain 480. Studies of food intake support that electrical stimulation of the anterior vagal nerve 460 can increase afferent traffic, which, in turn, influences function of satiety connections. At the central level, such electrical stimulation can decrease food intake and body weight.

Sensing Vagal Activity

While direct or indirect electrical nerve stimulation can achieve various effects (e.g., increase activity, selective activity, blocking of unidirectional or bidirectional nerve traffic, etc.), nerve fibers or bundles can also be monitored for activity. As already discussed, vagal afferents are integral part of a negative feedback loop induced by constitution and size of food in GIT. A study by Krolczyk et al., "Encoding Meal in Afferent Vagal Discharge", *J Physio. Pharma.,* 2004, 55, 1, 99-106, assessed vagal discharge in response to food and gastric distension in rats using a cuff electrode placed on the peripheral, afferent end of the right or left cervical vagus nerve at the level of the neck.

Data from the study showed that vagal input from the stomach code dynamic and static changes in response to gastric distension. In particular, the presence of food in duodenum elicited specific postprandial motility and activated vago-vagal reflexes to stimulate pancreatic secretion accompanied by a fall in plasma ghrelin and an increase of plasma leptin. The study noted that the chemical content of the food is most likely detected by duodenal nerve endings (chemoreceptors), whereas volume of a meal stimulates mechanoreceptors in upper gut, leading to distinct motility response.

The study of Krolczyk et al., noted other reports (using rat models) where a predominant nerve discharge comes from load sensitive mechanoreceptors of the stomach and that gastric volume more strongly signals for inhibition of food intake when compared to signaling by nutrient content.

In particular, the study of Krolczyk et al. showed that most intensive vagal response resulted from mechanical distension is induced by food intake; noting however, that there are significant differences in vagal activity related to chemical composition of given food. Thus, they concluded that not only size but also meal makeup influence food intake and that information related to size and makeup is at least partially encoded in vagal afferent discharge, beside the humoral signals.

More specifically, the study of Krolczyk et al., noted that the presence of chemically distinct food in the duodenum elicits clearly different afferent discharge in the vagus nerve and that two different patterns of vagal overall discharge are induced by food or gastric distension and those after meal are short lasting, which suggests a mechanism involving both signals from mechano- and chemoreceptors. The study concluded that food intake acts via neurohumoral routes of the brain-gut axis and that vagally mediated food induced negative satiety feedback loop acts via the following sequence of events: (i) size of meal in upper GIT (mechanoreceptors); (ii) chemical content in duodenum (chemoreceptors); and (iii) caloric load in liver (glucoreceptors).

With respect to actual signals sensed, the study noted that information collected form peripheral mechanoreceptors is encoded as combined amplitude-frequency and sequence spikes pattern in the vagus nerves only after short postprandial period. More specifically, left vagal afferents discharge rises with gastric distension of 6, 8 and 10 ml and were: 0.46+/−0.22 Hz, 0.65+/−0.31 Hz, 0.86+/−0.33 Hz respectively while similar discharge appeared in right vagal afferents: 0.41+/−0.08 Hz, 0.51+/−0.13 Hz and 0.77+/−0.27 Hz for 6, 8 and 10 ml of distension, respectively.

A, B and C Fibers

A nerve in the human body is typically composed of thousands of fibers, of different sizes, which may be designations by group (e.g., A, B and C). The vagus nerve, for example, may have approximately 100,000 fibers of various sizes (e.g., approximate diameters or cross-section) where each fiber can carry a signal. Normally, each axon (fiber) conducts in only one direction. Conduction velocity varies depending on size and other physiology such as myelination. The aforementioned A and B group fibers are myelinated, whereas C group fibers are unmyelinated.

Myelinated fibers are typically larger, conduct faster and have very low stimulation thresholds, compared to the unmyelinated type. Further, less energy is typically required to stimulate myelinated fibers, which exhibit a particular strength-duration curve that may relate to response for a given pulse width versus amplitude. In general, A and B group fibers can be stimulated with relatively narrow pulse widths (e.g., typically less than 1 ms). A group fibers conduct slightly faster than B group fibers and typically exhibit a slightly lower activation threshold. C group fibers are very small, conduct electrical signals very slowly, and have higher stimulation thresholds typically requiring a wider pulse width and higher amplitude for activation when compared to A and B group fibers. Hence, selective stimulation of only A and B group fibers may be achieved given appropriate equipment.

An exemplary method optionally includes control logic to classify sensed nerve activity where such classification may rely on groups such as A, B and C, myelinated/unmyelinated, etc. Activation of a nerve may rely on such classification. Activation may aim to transmit a signal or to block or inhibit a signal.

A study by Sengupta et al. ("Characteristics of vagal esophageal tension-sensitive afferent fibers in the opossum", *J. Neurophysiol.* (1989) 61(5):1001-1010) reported that esophageal distension was associated with an afferent vagal discharge rate of approximately 30-50 Hz. Primarily C-fibers and A-delta fibers (the latter being classified by the investigators as esophageal tension afferents with conduction velocities of 2.5-22 m/s) were found to mediate these impulses. The data may indicate that vagal modulation at these frequencies and a duration of ten seconds will approximate a physiological response to gastric distension.

As described herein, inhibition or blocking of signals of a vagus nerve may be used for treating or controlling a metabolic disorder (e.g., consider the eating disorder anorexia nervosa). Activation of a vagal nerve is accompanied by generation of a signal or signals, assuming the nerve or nerve fibers is/are not in a refractory phase. Some stomach signals are carried by C-fibers, which become refractory if stimulated at high frequency (e.g., about 40 Hz or higher) for more than a period of 30 to 60 seconds. Thus, an exemplary method may aim to inhibit or block C-fiber transmission by through use of a scheme that delivers energy using a high frequency with a certain "on" time followed by an "off" time (e.g., consider about 300 seconds on followed by about 20 seconds). This scheme could be repeated for the interval of time that control (blocking of the C-fiber information) is desired to be exercised.

An alternative scheme may consider that C-fibers become refractory if stimulated for a sufficiently long period. Thus, an alternative scheme may continuously stimulate the C-fibers to render them refractory and thereby block nerve signal transmission. Again, various gut signals (e.g., stomach) are carried by C-fibers, hence, such blocking schemes may be appropriate on a continuous, a periodic or an as desired/needed basis (e.g., in response to an event, a signal, a schedule, etc.). C-fibers conduct more slowly than A and B-fibers; an exemplary scheme may account for such conduction differences, particularly when blocking certain C-fiber signals.

Energy Mechanisms—Thermogenesis

While various chemical and mechanical mechanisms have been discussed, other mechanisms such as so-called energy mechanisms exist. Evidence suggests that core temperature is involved in the termination of feeding. For example, an animal may eat to keep warm and stop eating to prevent hyperthermia. Trends show that eating commences shortly after temperature starts to rise and that eating terminates in association with a temperature peak. For example, evidence shows that a liver temperature of about 39.3° C. is associated with end of a meal.

Evidence exists that a mechanism in the liver is able to signal an elevation in core temperature, thereby suggesting a neural inhibition of feeding when temperature increases. Further reduced thermogenesis due to a lower liver temperature causes a delay in the termination of feeding (noting that diabetic subjects show a reduced thermogenic response to a glucose or insulin infusion compared to their controls—The question rises if modified vagal signaling also affects glucose homeostatic mechanisms). As reported in the dissertation by van de Wall, a study found that feeding was inhibited after application of external heat to the liver.

Subdiaphragmatic denervation of the liver 460 abolishes this inhibition in food intake indicating the involvement of the hepatic vagal afferent 465 in this mechanism. Thus, all these studies demonstrate that there is a strong relation between (liver) temperature and meal termination and suggest that vagal afferents are important in thermosensitivity.

With respect to specific vagal pathways, a study by Zhang et al., "Thermosensitive transient receptor potential channels in vagal afferent neurons of the mouse", *Am J Physiol Gastrointest Liver Physiol* 286: G983-G991, 2004, demonstrates that afferent fibers in the hepatic branch of the vagus 465 are thermosensitive. More specifically, three types of thermosensitive unmyelinated fibers can be distinguished by cold (10° C. to 36° C.), warm (39° C. to 50° C.), and mixed (10° C. to 35° C. and 40° C. to 50° C.) temperatures, which suggests that the vagus nerve may mediate thermosensitivity.

Although in most experiments, the relation between satiety and thermogenesis is not directly studied, it could be that reduced thermogenesis in obese subjects causes a delay in satiety. One study found that in vagotomized rats the rise in thermic response following gastric intubation with a carbohydrate meal was diminished. Thus, it could be that a reduced afferent signaling could contribute to a decreased thermogenesis and thereby promoting obesity.

As described herein, various exemplary techniques optionally deliver energy to heat a vagal pathway and/or sense temperature. For example, in response to a decrease in liver temperature, one or more electrodes may be used to heat a vagal afferent or otherwise cause a response associated with an increased liver temperature.

Stimulation of Stomach

Various techniques exist for electrical stimulation of the stomach. Trials were performed using a canine model according to an exemplary arrangement 600 of FIG. 6 that included a proximal pair of electrodes 624 and a distal pair of electrodes 626 circumferentially positioned with respect to the stomach 420. Such an arrangement allows for delivery of energy to the stomach in a manner that accounts for transit time, direction, etc. For example, a timing sequence may call for delivery of energy to the proximal pair 624 and the distal pair 626 in a coordinated manner that facilitates emptying of the stomach 420. As described herein, energy delivered to the stomach may or may not cause contraction of stomach muscle. Energy insufficient to cause contraction of stomach muscle (e.g., due to delivery time, amplitude, frequency, etc.) may still, depending on conditions, lead to weight loss.

For various trials, the distal pair of electrodes 626 was configured in a bipolar manner for deliver energy to the stomach 420. A device 628 that included a timing mechanism and a power source was used to control delivery energy to the stomach 420 via the distal electrodes 626. Various trials used a pulse train with biphasic pulses delivered at a frequency of about 50 Hz, a duty cycle of about 100% and a per phase width of about 10 ms for a pulse width of about 20 ms. Various pulse train durations were used, generally in a range from about 4 seconds to about 6 seconds.

As C-fibers tend to respond more readily to stimulation with longer pulse width, pulse width was limited for delivery energy to the stomach. However, where C-fiber activation is desired, pulse width may be adjusted accordingly. As described herein, where an exemplary method aims to activate stomach muscle, a delivery scheme can use energy delivery parameters that aim to minimize effect on C-fibers. Such a scheme may, for example, minimize pain associated with C-fibers, accommodation or adaptation of C-fibers, etc.

As described herein, various exemplary techniques include delivery of energy to the stomach using a pulse width less than 20 ms. For example, a pulse train may use biphasic pulses with a phase width of about 1 ms (pulse width about 2 ms) and a delivery frequency of about 500 Hz to achieve a duty cycle of about 100%. In such an example, the shorter pulse width (and phase width) reduces activation of C-fibers while the high duty cycle ensures activation of stomach muscle or a beneficial affect on the stomach for purposes of controlling metabolism and/or feeding.

Table 1, below, provides examples of delivery schemes (S1 through S7) with reference to vagal activation and stomach muscle activation for various times (Time 1 through Time 4). The scheme S1 delivers energy in a manner that aims to primarily activate stomach muscle while the scheme S2 delivers energy in a manner that aims to primarily activate vagal nerves. In contrast, schemes S3-S7 deliver energy in a manner that aims to activate both stomach muscle and vagal nerves.

TABLE 1

Delivery Schemes

|    | Time 1 | Time 2 | Time 3 | Time 4 |
|----|--------|--------|--------|--------|
| S1 | S      | S      | S      | S      |
| S2 | V      | V      | V      | V      |
| S3 | S      | V      | S      | V      |
| S4 | S + V  | S      | S + V  | S      |
| S5 | S + V  | V      | S + V  | V      |
| S6 | S + V  | S + V  | S + V  | S + V  |
| S7 | S + V  | S      | V      | S + V  |

As noted in schemes S4-S7, energy may be delivered in a manner that aims to activate both stomach muscle and vagal nerves at a particular time (e.g., using different electrodes, at least one common electrode, the same electrodes). Such schemes are discussed in more detail with respect to plots of FIG. 8. Overall, if a method aims to affect, at some point in time, the stomach muscles only, then a delivery scheme may be selected that minimizes its effect on C-fibers. Such a method may aim to reduce activation of C-fibers by reducing charge density delivered per pulse. In particular, the pulse width of the energy may be limited to a short duration (e.g., about 1 ms). Further, a delivery scheme that reduces charge density can reduce tissue damage. Yet further, in the scheme S3, where a particular region or site is used for both stomach and vagal activation, vagal nerves may be more responsive to delivered energy for Time 2 and Time 4 because they are not activated during Time 1 and Time 3. Thus, selective activation can enhance control or effectiveness of various schemes that aims to activate stomach muscle and vagal nerves.

In various trials, energy was delivered to a pair of distal electrodes 626 using a constant current, biphasic delivery scheme. Constant current refers to the current value during a particular phase of a pulse or, for example, to the peak-to-peak current for a biphasic pulse. Trials used different currents, typically in a range of about 2 mA to about 40 mA peak-to-peak. The delivery scheme used for the trials aimed to distribute energy by reducing the charge density delivered per pulse, which, again, included use of a limited pulse width.

Various trials used the arrangement 600 and delivery schemes with pulse widths less than 10 ms. An exemplary scheme used a biphasic pulse with a per phase width of about 1 ms delivered at a frequency of about 400 Hz. This scheme resulted in a desired effect on the stomach. With respect to contraction of stomach muscle, duty cycles were calculated using the following equation: Duty Cycle (%)=Pulse Width per Phase (s)*No. of Phases*Frequency (Hz). Thus, for pulse train with a biphasic pulse and a pulse width of 1 ms, delivered at 400 Hz, the duty cycle was 80%. With respect to train duration, a train may be delivered for about 1 s to about 20 s.

Various exemplary methods may include delivery schemes according to one or more parameter settings or values selected from the ranges below:

| | |
|---|---|
| Energy Injection Mode: | Constant Voltage or Constant Current |
| Pulse Amplitude: | ~0 V to 16 V peak-to-peak |
| | ~0 mA to 40 mA peak-to-peak |
| Pulse Width (per phase): | ~10 □s to 10 ms |
| Frequency (of train): | ~0 Hz to 500 Hz |
| Pulse Morphology: | Biphasic (active or capacitive) |
| Duty Cycle: | ~0% to 100% |

Figure 6:
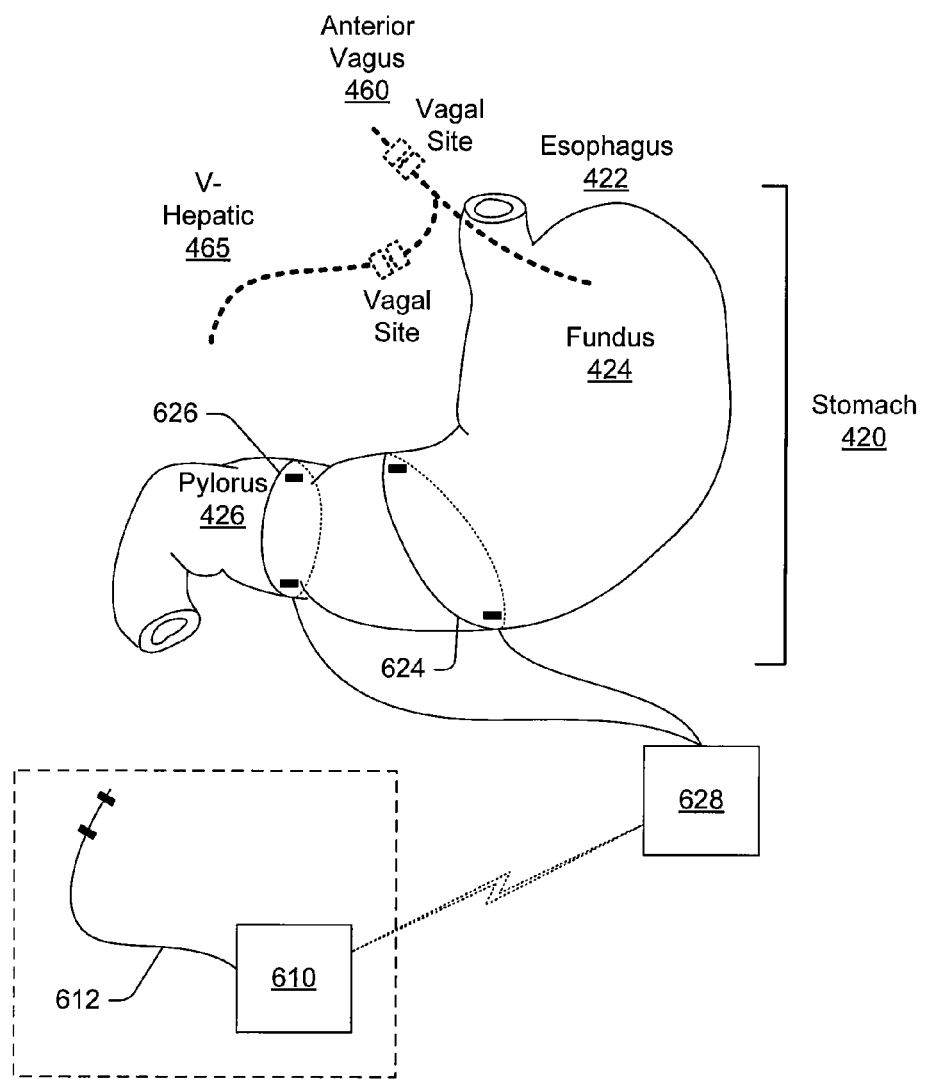
FIG. 6 is a diagram of an exemplary stimulation arrangement that includes two implantable devices where one of the devices provides for stimulation of the stomach.

The exemplary arrangement 600 of FIG. 6 optionally includes an implantable device 610 that includes one or more electrode bearing leads 612. According to the exemplary arrangement 600, the device 610 and the device 628 may communicate uni- or bi-directionally. The device 610 may include features of the devices 110, 112, 114, 118 of FIG. 1 and/or the device 200 of FIG. 2. For example, the device 610 may include features for stimulation of a vagal nerve and optionally perform such stimulation in a manner coordinated with stomach stimulation.

FIG. 6 also shows two possible vagal activation locations. One location is on the anterior vagus 460 prior to the hepatic branch 465 and/or the pyloric branch 468 (see FIG. 4). While the dashed lines indicate electrode pairs, one or more electrodes may be located at either location. The electrodes may be associated with a stomach activation device (e.g., the device 628), a dedicated vagal activation device (e.g., the device 610), or any appropriate device capable of delivering activation energy to the vagal nerve.

An exemplary method for delivering energy for vagal nerve activation includes use of a delivery scheme where one or more parameter values are selected from the ranges below:

| | |
|---|---|
| Pulse Amplitude: | ~0 mA to 10 mA per phase |
| Pulse Width (per phase): | ~100 □s to 1 ms |
| Frequency (of train): | ~0 Hz to 100 Hz |
| Pulse Morphology: | Biphasic (active or capacitive) |
| Duty Cycle: | ~0% to 100% |

Various exemplary methods disclosed herein optionally include delivery of energy to smooth muscle of at least a portion of the GIT where the portion of the GIT defines a longitudinal axis extending therethrough. Such delivery of energy may include delivery at a proximal location to the smooth muscle circumferentially about the portion of the GIT in a plane (e.g., substantially perpendicular) intersecting the longitudinal axis where the energy is sufficient to activate the smooth muscle to produce a local circumferential contraction at the proximal location. Such exemplary methods may optionally include delivery of energy to at least one distal location to the smooth muscle circumferentially about the portion of the GIT in a plane (e.g., substantially perpendicular) intersecting the longitudinal axis where the energy is sufficient to activate the smooth muscle to produce a local circumferential contraction at the distal location. Further, such optional delivery of energy may include phase-locking such that the energy is delivered at the proximal and distal locations successively and repetitively.

Exemplary Techniques for Adjusting Food Intake

Figure 7:
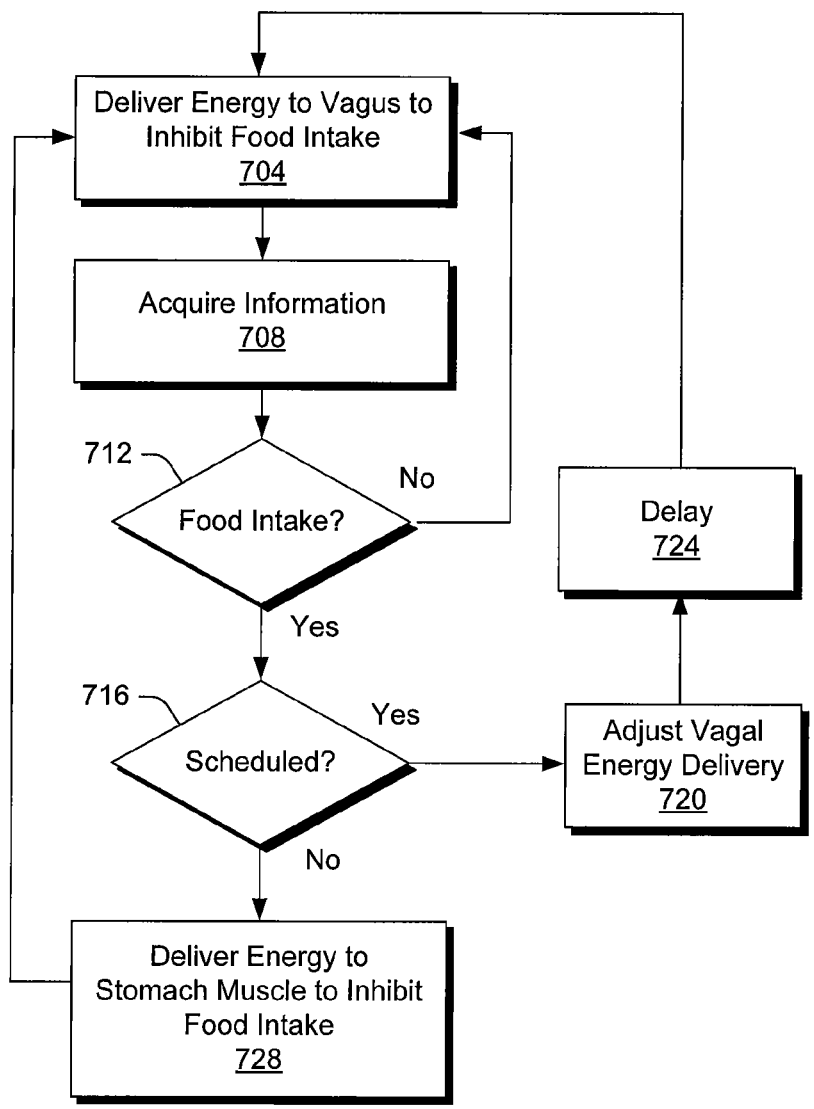
FIG. 7 is a block diagram of an exemplary method for delivering stimulation to affect food intake.

FIG. 7 shows a block diagram of an exemplary method 700 for inhibiting food intake. The various blocks are optionally in the form of control logic instructions storable in memory and operable in conjunction with a processor.

The method 700 includes a delivery block 704 that calls for delivery of energy to the vagus to inhibit food intake. An acquisition block 708 may operate concurrent with any of the other blocks or alone. The acquisition block 708 acquires information related to food intake, for example, via an implantable sensor and/or an external sensor. The method 700 uses the acquired information in a decision block 712 that decides whether food intake is occurring. If the decision block 712 decides that food intake is not occurring, then the method 700 continues at the delivery block 704; however, if the decision block 712 decides that food intake is occurring, then the method 700 continues at another decision block 716.

The decision block 716 decides if the food intake that is occurring is scheduled according to a pre-programmed schedule or events that have decided that food intake should occur. If the decision block 716 decides that the food intake is scheduled (e.g., diurnal or other schedule), then the method 700 enters an adjustment block 720 that adjusts one or more of the vagal energy delivery parameters to account for scheduled food intake. For example, the vagal energy delivery may be turned off. Thereafter, the method 700 enters a delay block 724 that causes a delay before resetting the vagal energy delivery per the delivery block 704. However, if the decision block 716 decides that the food intake is not scheduled, then a delivery block 728 follows that calls for delivery of energy to stomach muscle to, for example, inhibit food intake or to clear the stomach via contractions. The method 700 may return to the delivery block 704 and proceed as appropriate.

In general, the exemplary method 700 can provide low energy vagal activation and higher energy stomach muscle activation in a manner that conserves power of one or more implantable devices. The exemplary method 700 may be implemented using one or more implantable devices and optionally one or more external devices (e.g., to acquire information, etc.).

With respect to the delivery block 728, this block may call for delivering energy to the distal antrum using a single bipolar electrode with anode and cathode placed circumferentially about 180 degrees apart, using energy delivery parameters such as those discussed with respect to FIG. 6. The delivery block 728 may optionally call for delivery of energy, for example, to cause contractions of the stomach that propagate distally. With respect to the delivery block 704, this block may call for stimulating the left vagus using stimulation parameters such as those discussed with respect to FIG. 6.

The exemplary method 700 may call for stomach activation to elicit contractions when the patient is eating, and activation to elicit neural afferents without contractions when the patient is fasting.

Figure 8:
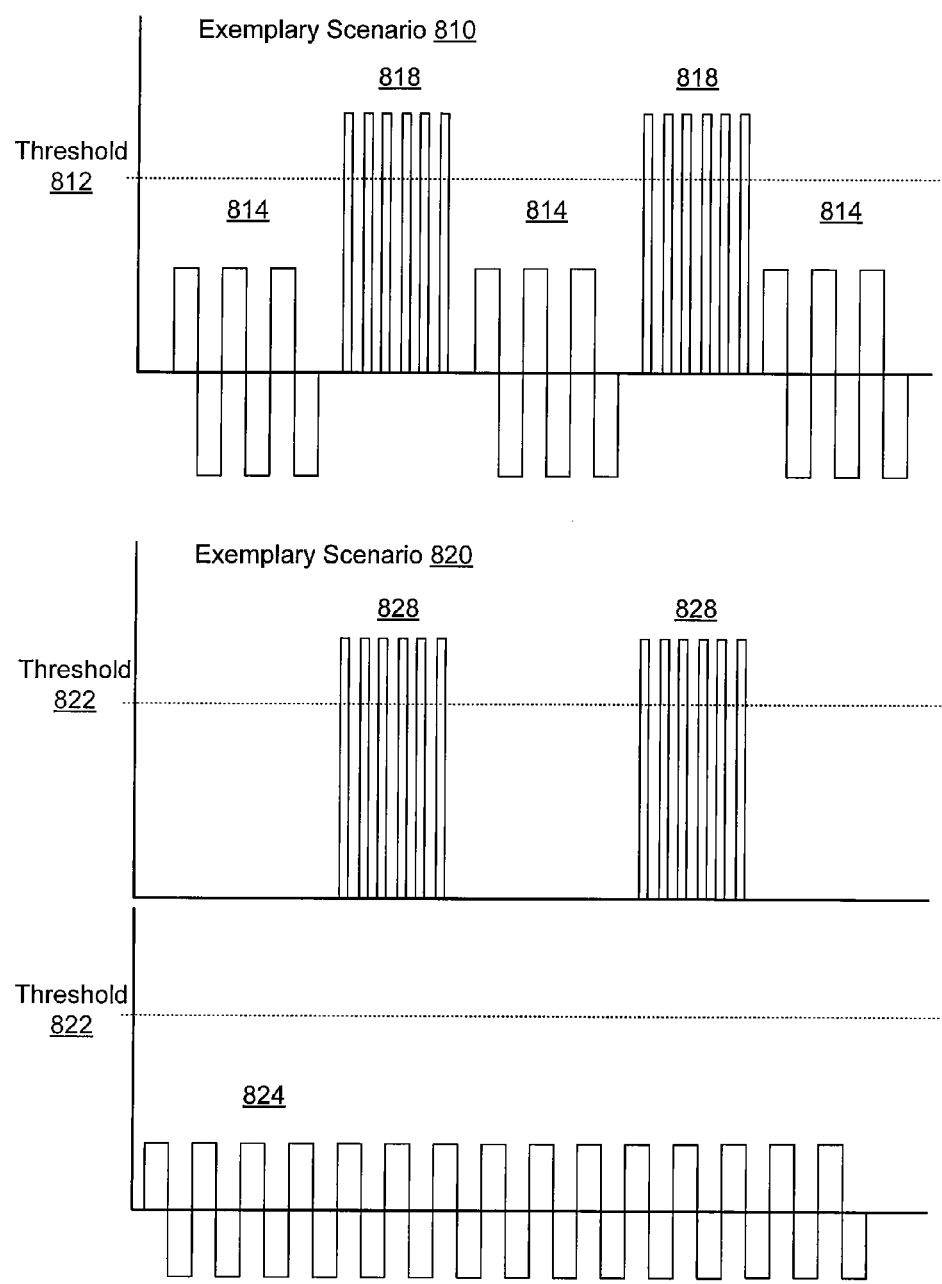
FIG. 8 is a series of plots that illustrate two scenarios whereby stimulation energy is delivered supra-threshold and/or sub-threshold.

FIG. 8 shows two exemplary scenarios 810, 820 for activation with respect to one or more thresholds 812, 822. While a threshold accounts for a complete set of stimulation parameters that are required to invoke the desired physiological effect, the scenarios 810, 820 address a limited set of parameters and, in particular, use amplitude to illustrate how parameters may be used to selectively activate tissue (e.g., nerves, stomach muscle, etc.). With respect to a 'threshold" for initiating an action potential on an excitable membrane, strength-duration curve, amplitude and pulse width are typically important parameters, however, the concept of a threshold for obtaining a desired physiological effect can include these parameters and may extend to others. Again, delivery of sub-threshold (conventional threshold) energy to a nerve and delivery of sub-threshold (conventional threshold) energy to a muscle may still result in a desired effect as described herein. Hence, such energy would be considered, conventionally, sub-threshold but at or above threshold for the desired effect.

Factors affecting threshold can include frequency of delivered energy, frequency of activation (e.g., nerve activation or muscle contraction) and burst duration. Pulse morphology can also be a consideration as a desired effect may depend on activation of particular fiber populations (a, b, C-fibers, etc.).

The scenario 810 may be used to deliver energy to a muscle and to one or more nerves (e.g., branch, nerve plexus, etc.). In this scenario, a threshold 812 exists that corresponds to the threshold required for stimulation of muscle (e.g., stomach muscle). Thus, the energy 818 is supra-threshold and aimed at stimulating muscle. In contrast, the energy 814 is sub-threshold and aimed at another result. For example, the sub-threshold energy 814 may be appropriate to activate vagal afferents or to block vagal afferents (see, e.g., schemes of Table 1).

As already discussed, C-fibers typically respond to energy delivered using a wider pulse width. Thus, an exemplary method may call for delivery of supra-threshold stimulation energy and call for delivery of sub-threshold stimulation energy where the sub-threshold stimulation energy causes a physiological response. Or, in other words, the energy 818 is supra-threshold for a particular purpose and the energy 814 is supra-threshold for another purpose. Noting that due to factors such as pulse width, the energy 818 may be supra-threshold for one purpose and sub-threshold for another purpose.

Consider an example using one or more of the electrode arrangements shown in FIG. 6. The higher amplitude, narrower pulse width energy 818 may cause contractions of the stomach 420 while the lower amplitude, wider pulse width energy 814 may cause an increase in vagal afferent 460 traffic to the brain 480. Thus, the scenario 810 may be used to coordinate actions to achieve a desired response with respect to patient food intake (see, e.g., schemes of Table 1 with S, V, S, V timings).

An exemplary device optionally includes a learning algorithm whereby the threshold 812 is determined once, periodically or as needed. Further such a device may acquire information as to activation of vagal afferents (e.g., via one or more physiological sensors) to establish another threshold, which serves a different purpose that the threshold 812.

As disclosed herein, parameters used for vagal afferent activation can selectively determine a desired effect. Consider the aforementioned rabbit and swine studies whereby the same parameters resulted in different effects for rabbit (weight reduction) and swine (increased systemic gastrin and insulin). Thus, an exemplary scenario may optionally include two or more thresholds where one corresponds to muscle stimulation, one corresponds to vagal afferent stimulation sufficient to decrease food intake or weight reduction and one corresponds to stimulation to increase gastrin, insulin, etc.

The exemplary scenario 820 includes a threshold 822 and separate channels where one channel calls for delivery of supra-threshold stimulation energy 828 and where one channel calls for delivery of sub-threshold stimulation energy 824. Yet, the energy 824 may be supra-threshold for another purpose. These channels may be implemented in a single implantable device or in separate implantable devices (see, e.g., the devices of FIG. 1, the device 200 of FIG. 2, etc.). As shown in FIG. 8, pulses may be multi-phasic (e.g., bi-phasic pulses 814, 824). While the pulses are shown as square pulses, a pulse may have a different shape, for example, where amplitude decays over time (e.g., consider a tilt).

An exemplary method includes calling for delivery of supra-threshold energy by a first implantable device for a particular purpose and calling for delivery of sub-threshold energy by a second implantable device, which is typically supra-threshold for another purpose. In this example, the devices optionally operate in a coordinated manner facilitated by uni- and/or bi-directional communication circuits. Alternatively, or in addition to, one or both device may optionally sense delivery of energy by the other device or a signal related thereto. For example, if a device that delivers sub-threshold energy fails, the lack of an electrical signal related to or stemming from the sub-threshold energy may be sensed by the other device. In response, the other device may signal or alert a patient or care provider as to the condition of the failed device.

The scenario 810 and/or the scenario 820 may be used in an exemplary method that calls for delivery of energy on the surface of the stomach at two different frequencies in order to elicit a local nerve plexus of the stomach (e.g., without resulting muscle contraction) and to elicit organ muscle contraction.

In a specific example, stomach stimulation occurs at a frequency of about 500 Hz using rectangular biphasic pulses with per phase width of about 1 ms and an amplitude of about +/−8 V. Such energy may be delivered in bursts (e.g., about 5 s on and about 5 s off) over about 10 minutes to 20 minutes when desired.

In a specific example, vagal activation occurs using rectangular biphasic pulses with per phase width of about 500 microseconds, a current of about 0.01 mA to about 3.5 mA and a frequency of about 30 Hz. Such energy may be delivered in bursts (e.g., about 30 s on and about 180 s off) where the energy may be delivered substantially all day (e.g., 24 hours a day).

In a specific example, an exemplary device includes circuits to deliver constant voltage and constant current. For example, such a device may deliver constant voltage energy to the stomach for muscle stimulation and deliver constant current energy to a vagal nerve.

Figure 9:
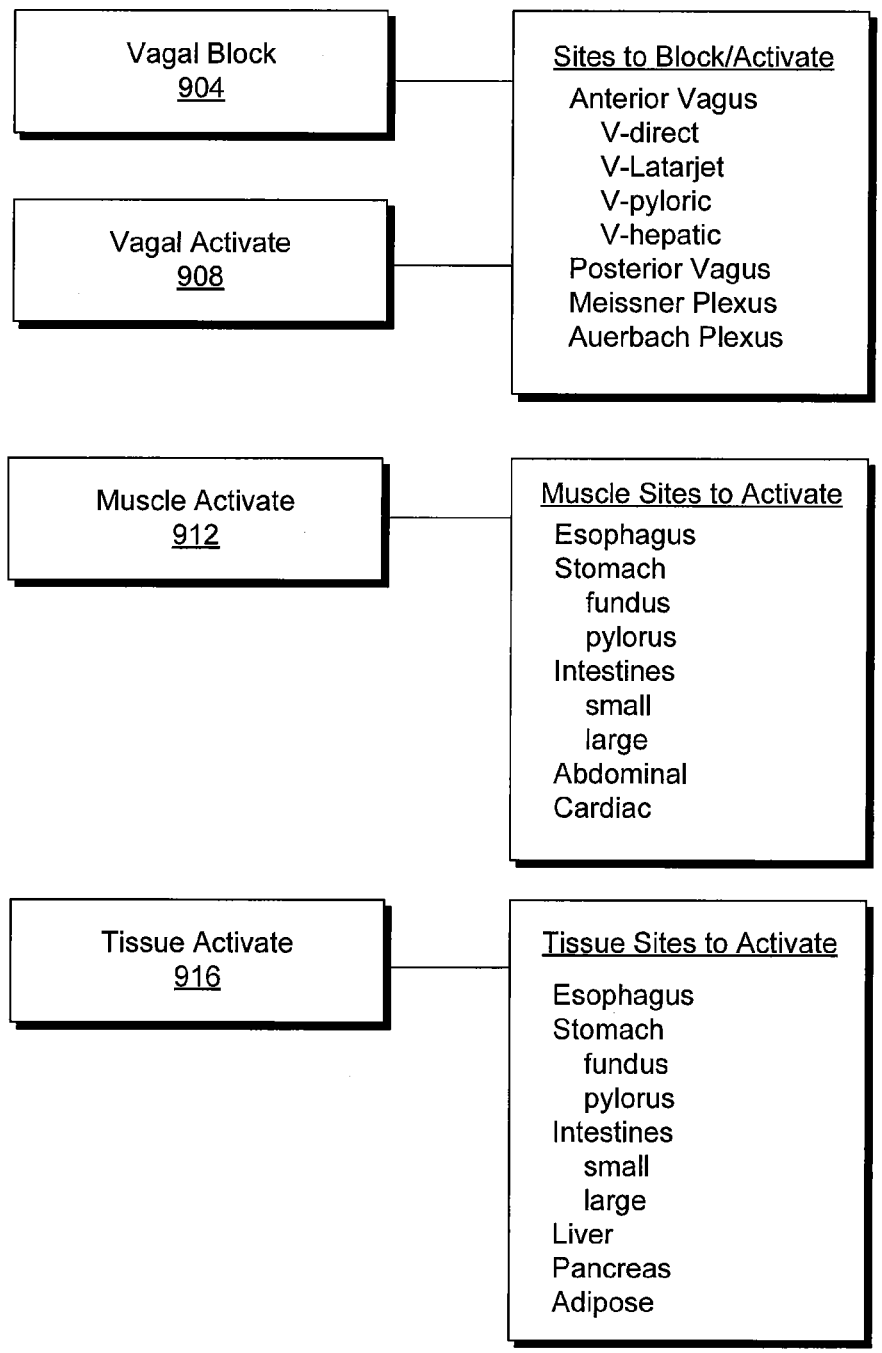
FIG. 9 is a diagram of exemplary modules for calling for action related to nerve activation/blocking, muscle activation and tissue activation.

FIG. 9 shows various action modules that may be used in conjunction with one or more implantable device. Such modules may be in the form of instructions storable in memory of a device and operable using a processor (e.g., a microprocessor). Such modules may be or form control logic for operation of an implantable device.

A vagal block module 904 operates to call for delivery of electrical energy to one or more sites. For example, the module 904 may call for delivery of stimulation energy to block action potentials traveling (uni- or bi-directionally) in the anterior vagus (V-direct, V-Latarjet, V-pyloric, V-hepatic, etc.), the posterior vagus, the Meissner plexus or the Auerbach plexus.

A vagal activate module 908 operates to call for delivery of electrical energy to one or more sites. For example, the module 908 may call for delivery of energy to generate action potentials traveling (uni- or bi-directionally) in the anterior vagus (V-direct, V-Latarjet, V-pyloric, V-hepatic, etc.), the posterior vagus, the Meissner plexus or the Auerbach plexus.

A muscle activate module 912 operates to call for delivery of electrical energy to one or more sites. For example, the module 912 may call for delivery of energy to activate the esophagus, the stomach (e.g. fundus, pylorus, etc.), the intestines (small and/or large), one or more abdominal muscles or the myocardium.

A tissue activate module 916 operates to call for delivery of electrical energy to one or more sites. For example, the module 916 may call for delivery of energy to activate the esophagus, the stomach (e.g., fundus, pylorus, etc.), the intestines (small and/or large), the liver, the pancreas, adipose tissue. In general, the tissue activate module 916 aims to activate such tissue in a manner to cause a physiological response other than contraction of a muscle.

Other modules may also be used. For example, a CNS module or SNS module may be used to activate and/or block activity of the CNS or the SNS. For example, a module directed to the splanchnic nerve (see, e.g., nerve 470 of FIG. 5) may be used to elicit appropriate responses. Further, stimulation (activation and/or blocking) may occur through use of near-field and/or far-field delivery of energy. For example, a pair of electrodes place remote from a particular nerve may be able to generate a field that propagates in the body and thereby activates the nerve. Further, such a far-field approach may activate a certain type of nerve based on parameters associated with the delivered energy (e.g., amplitude, frequency, pulse width, etc.).

An exemplary method includes 24 h gastric and 24 h vagal activation whereas another exemplary method includes 24 h vagal and 12 h gastric activation.

Figure 10:
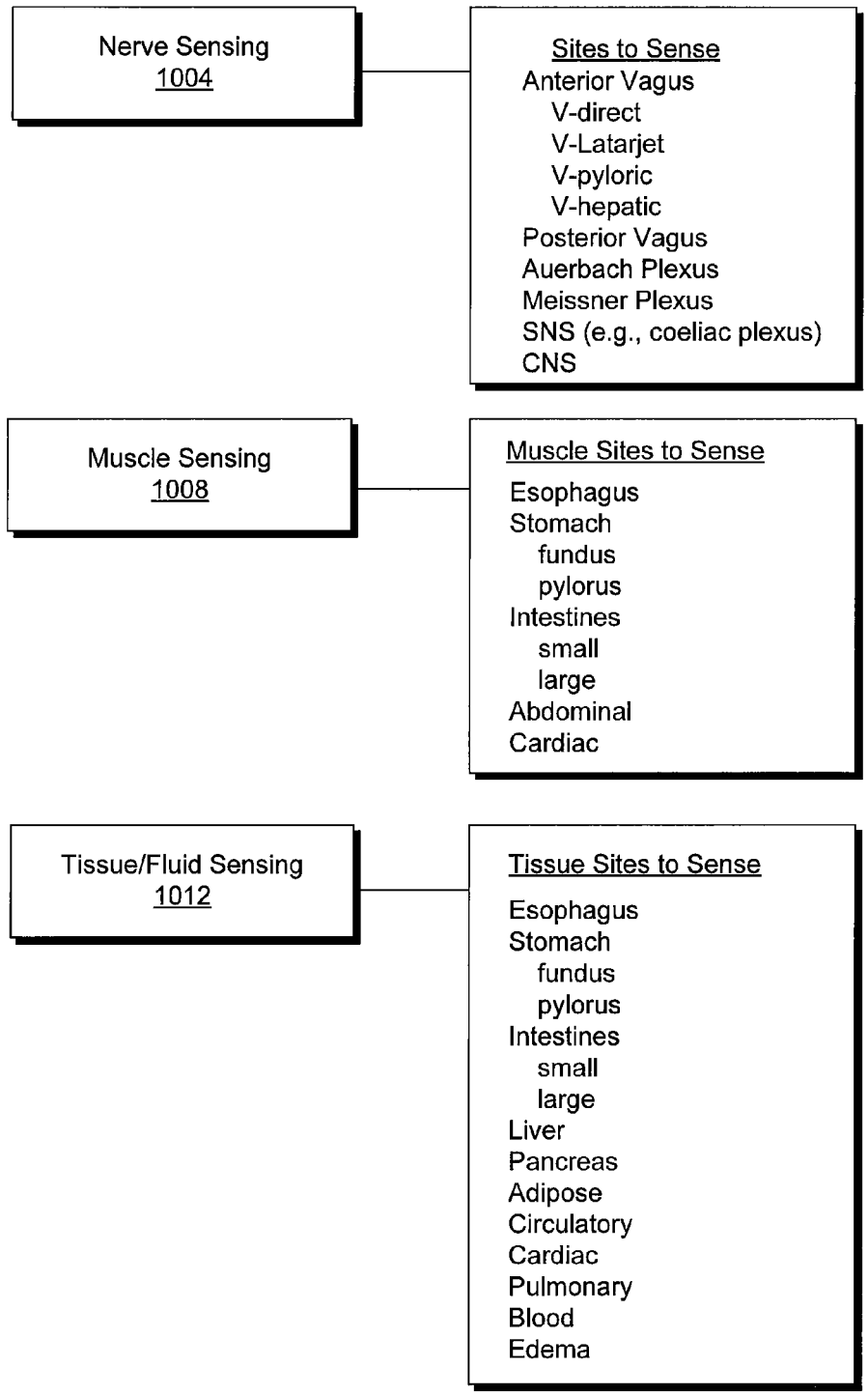
FIG. 10 is a diagram of exemplary modules for calling for action related to sensing nerve activity, muscle activity and tissue and/or fluid physiology.

FIG. 10 shows various action modules that may be used in conjunction with one or more implantable device. Such modules may be in the form of instructions storable in memory of a device and operable using a processor (e.g., a microprocessor). Such modules may be or form control logic for operation of an implantable device.

In general, the modules of FIG. 10 call for sensing physiological information. For example, the module 1004 pertains to nerve sensing. Such a module may call for sensing nerve information at one or more sites such as at the anterior vagus (V-direct, V-Latarjet, V-pyloric, V-hepatic, etc.), at the posterior vagus (efferent preganglionic fibers mainly to the posterior surface of the stomach), at the Auerbach plexus (e.g., tonic and rhythmic contractions), at the Meissner plexus (e.g., blood flow), at any SNS nerve (e.g., coeliac plexus), or at any CNS nerve.

A module 1008 pertains to muscle sensing. For example, the module 1008 may call for sensing activity at one or more muscle sites such as at the esophagus, at the stomach (fundus, pylorus, etc.), at the intestines (small and/or large), at the abdominal muscles, or at the myocardium.

A module 1012 pertains to tissue and/or fluid sensing. For example, such a module may call for sensing a physiological parameter associated with tissue and/or fluid. As already mentioned, liver temperature varies with respect to food intake; thus, such a module may call for sensing liver temperature. Also consider sensing at sites such as the esophagus, the stomach (fundus, pylorus, etc.), the intestines (small and/or large), the pancreas, adipose tissue, circulatory system sites, cardiac sites, pulmonary sites, sensing for edema at one or more sites, etc.

Figure 11:
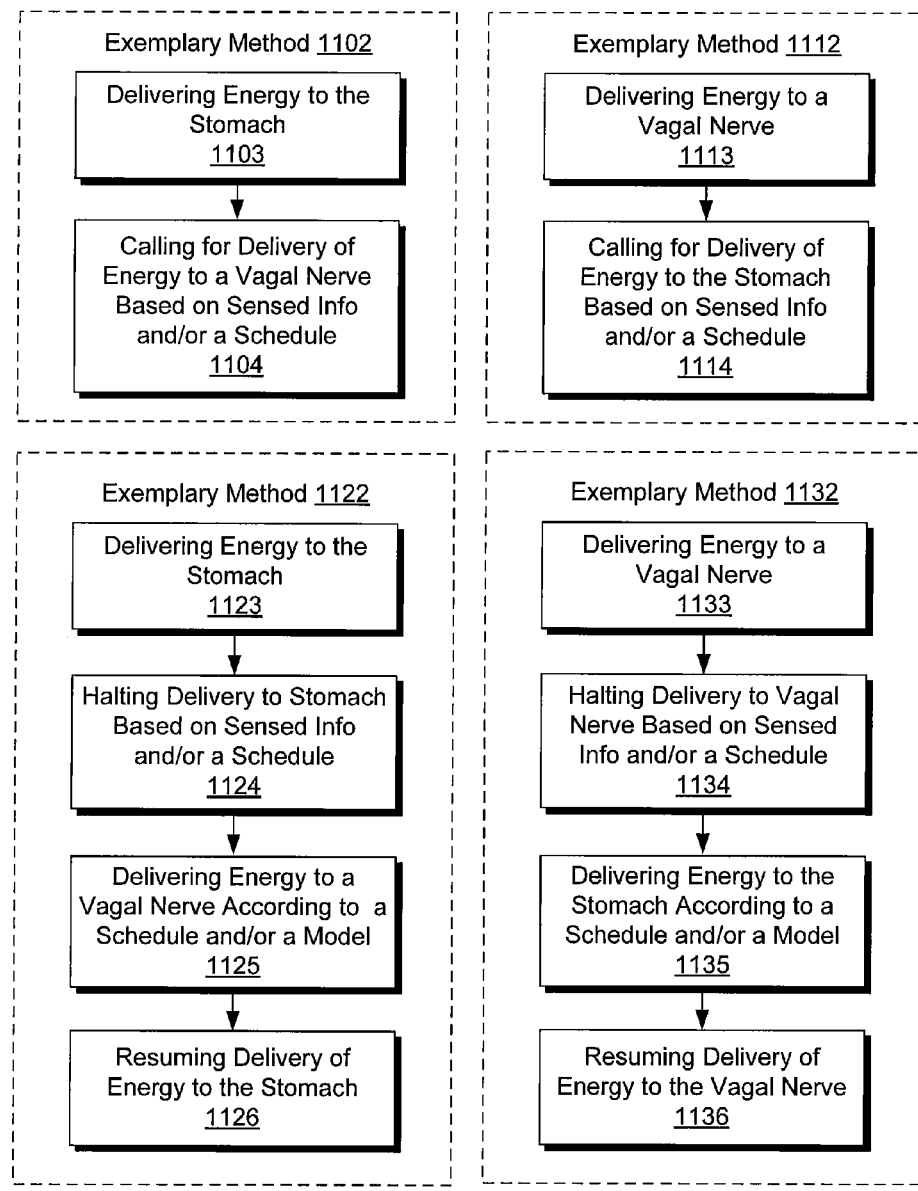
FIG. 11 is a block diagram of various exemplary methods that may be optionally implemented using one or more of the exemplary devices described herein.

FIG. 11 shows various exemplary methods 1100 that include delivering energy to the stomach and delivering energy to a vagal nerve according to sensed information, a schedule, or a model. An exemplary model may account for device characteristics as well as sensed information, a schedule, etc., to determine when, where or how to deliver energy to the stomach and/or a vagal nerve.

An exemplary method 1102 includes delivering energy to the stomach 1103 and at some point in time calling for delivery of energy to a vagal nerve based on sensed information and/or a schedule 1104. An exemplary method 1112 includes delivering energy to a vagal nerve 1113 and at some point in time calling for delivery of energy to the stomach based on sensed information and/or a schedule 1114. In the methods 1102 and 1112, the sensed information may include any of the sensed information of FIG. 10 (e.g., nerve 1004, muscle 1008 and/or tissue/fluid 1012) and the schedule may be a feeding schedule, a patient activity schedule, etc. In the methods 1102 and 1112, delivery of energy or calling for delivery of energy may include energy to activate or block per the various examples of FIG. 9 (e.g., vagal block 904, vagal activate 908, muscle activate 912, tissue activate 916).

An exemplary method 1122 includes delivering energy to the stomach 1123 and halting delivery of the energy to the stomach (or adjusting) based on sensed information and/or a schedule 1124. In turn, the method 1122 delivers energy to a vagal nerve according to a schedule and/or a model 1125. For example, sensed information may cause the halting 1124 and then cause a model to call for the delivering 1125. In another example, the halting 1124 and the delivering 1125 may both occur according to a schedule (e.g., feeding schedule, etc.). The method 1122 further includes resuming delivery of energy to the stomach 1126, which may occur automatically following the delivering 1125. For example, where a schedule calls for delivery of energy to a vagal nerve for a period of time, upon expiration of the time period the method 1122 may resume delivery of energy to the stomach and the delivering may use one or more different energy delivery parameters (i.e., different than for the delivering 1123). For example, delivery of energy may occur at a different stomach site, a different energy level, a different frequency, etc.

An exemplary method 1132 includes delivering energy to a vagal nerve 1133 and halting delivery of the energy to a vagal nerve (or adjusting) based on sensed information and/or a schedule 1134. In turn, the method 1132 delivers energy to the stomach according to a schedule and/or a model 1135. For example, sensed information may cause the halting 1134 and then cause a model to call for the delivering 1135. In another example, the halting 1134 and the delivering 1135 may both occur according to a schedule (e.g., feeding schedule, etc.). The method 1132 further includes resuming delivery of energy to the vagal nerve 1136, which may occur automatically following the delivering 1135. For example, where a schedule calls for delivery of energy to the stomach for a period of time, upon expiration of the time period the method 1132 may resume delivery of energy to the vagal nerve and the delivering may use one or more different energy delivery parameters (i.e., different than for the delivering 1133). For example, delivery of energy may occur at a different vagal nerve site (e.g., same nerve or different nerve), a different energy level, a different frequency, etc.

Referring again to the exemplary scenarios 102, 104 and 106 of FIG. 1, such scenarios optionally include sensing using one or more of the sensing modules 1004, 1008, 1012 and optionally include acting using one or more of the action modules 904, 908, 912. Further, the actions may depend on information acquired via sensing or information acquired by communication with an external device (e.g., the device 116). The exemplary scenarios 102, 104 and 106 may be used to implement one or more of the exemplary methods 1100 of FIG. 11.

Overall, the exemplary scenarios 102, 104, 106 aim to increase therapeutic results. In particular, a need exists for increasing the response rate beyond that for patients fitted with a single device that delivers a single type of therapy (e.g., vagal activation only or stomach activation only). The exemplary techniques disclosed herein aim to achieve a higher response rate through an increased number of available therapies and/or through coordinated action of a plurality of implantable devices.

An exemplary method for treating an eating or metabolism disorder includes calling for delivery of energy to the stomach using a pulse train that includes use of pulses with a pulse width less than approximately 20 ms, a duty cycle greater than approximately 20% and a pulse train duration of less than approximately 10 seconds and calling for delivery of energy to a vagal nerve (see, e.g., methods 1100 of FIG. 11). Such an exemplary method may include use of a pulse train duration greater than approximately 2 seconds. Such an exemplary method may include use of biphasic pulses where, for example, each phase of a biphasic pulse has a width of less than approximately 10 ms. While biphasic pulses are mentioned, other types of waveforms may be used. For example, multiphasic pulses may be used where each phase of a multiphasic pulse optionally includes use of a phase width of less than approximately 10 ms.

With respect to delivery of energy to the stomach, as mentioned with respect to FIG. 6, a bipolar electrode configuration may be used, hence, the calling of the aforementioned exemplary method may call for delivery of energy to the stomach using a bipolar electrode configuration.

While various pulse widths and frequencies have been mentioned, various trials indicate that duty cycles greater than a certain percentage enhance results stemming from delivery of energy to the stomach. Thus, pulse width and frequency may be selected with respect to a duty cycle criterion. Further, pulse width may be selected with respect to a C-fiber activation criterion (e.g., to minimize C-fiber activation when delivering energy to the stomach). In general, pulse frequency of a pulse train may range from approximately 1 Hz to approximately 1000 Hz.

Various exemplary methods include delivering a pulse train to the stomach that uses pulses with a phase width less than approximately 10 ms reduces risk of C-fiber activation, reduces pain, reduces nociception, etc. Pain is a combination of sensory (discriminative) and affective (emotional) components. The sensory component of pain is defined as nociception and primary nociceptive afferents include C-fibers (and A☐-fibers). Hence, delivering a pulse train that uses pulses with a phase width less than approximately 10 ms may be expected to reduce C-fiber mediated pain, noting that delivering a pulse train that uses pulses with a phase width less than approximately 10 ms may reduces risk of adverse effects. For example, a short pulse width may reduce charge density to a level that reduces risk of tissue damage. An exemplary method may include calling for delivery of energy to the stomach using a pulse train that comprises pulses with a phase width less than approximately 10 ms to reduce risk of vomiting and vomiting.

With respect to possible delivery sites or regions of the stomach, an exemplary method may include calling for delivery of energy to the distal antrum proximate to the pylorus or pre-pyloric region of the stomach (see, e.g., FIG. 9). An exemplary method may include calling for delivery of energy to the superior margin of the lesser curvature of the stomach and the inferior margin of the greater curvature of the stomach. More generally, an exemplary method may call for delivery of energy to the duodenum, the large intestine, the pylorus, the fundus, the fundus and the pylorus, etc. An exemplary method may call for delivery of energy to the stomach sequentially, for example, to the fundus and then to the pylorus.

With respect to possible delivery sites or regions of the vagus, an exemplary method may include calling for delivery of energy to a sub-diaphragmatic portion of the anterior vagus nerve. An exemplary method may include calling for delivery of energy to a hepatic branch, a Latarjet branch, a pyloric branch, a portion superior to the hepatic branch (see, e.g., FIG. 9).

Various exemplary methods may include calling for delivery of energy to one or more other nerves, organs, etc. For example, an exemplary method may call for delivery of energy to the stomach, a vagal nerve and the splanchnic nerve (see, e.g., FIG. 9). Delivery of energy to any of these nerves, organs, etc., may occur according to a schedule.

Various exemplary methods include calling for delivery of energy to the stomach in response to acquired information, for example, information sensed using an implantable sensor and/or information transmitted to an implantable device capable of calling for delivery of energy and/or delivering energy (see, e.g., methods 1100 of FIG. 11). An implantable sensor may sense electrical activity of the body (e.g., myocardial electrical activity, muscle electrical activity of a muscle of the gastric system, etc.), may sense mechanical activity of the body (e.g., mechanical activity of the gastric system, etc.), may sense chemical activity of the body (e.g., chemical activity of the gastric system, etc.).

With respect to delivery of energy to a vagal nerve, various exemplary methods may include calling for delivery of energy to a vagal nerve using a pulse width of approximately 100 microseconds to approximately 4000 microseconds. Such a method may include use of a multiphasic pulse, for example, where each phase of the multiphasic pulse includes a phase width of approximately 50 microseconds to approximately 2000 microseconds. Voltage of energy delivered to a vagal nerve may use a selected voltage level that does not cause vomiting.

Various exemplary methods may include calling for delivery of energy to a vagal nerve that blocks transmission of afferent nerve activity and/or efferent nerve activity. For example, a method may include calling for delivery of energy to a vagal nerve at a frequency greater than about 1 kHz to block transmission of nerve activity.

Various exemplary methods may include calling for delivery of energy to the stomach and calling for delivery of energy to a vagal nerve at different times and/or approximately simultaneously (see, e.g., methods 1100 of FIG. 11). Calling for delivery of energy to the stomach and/or the vagal nerve may occur according to a feeding schedule, a diurnal schedule, etc.

Various exemplary methods include delivering energy to the stomach using an implantable device and/or delivering energy to a vagal nerve using an implantable device. Various exemplary methods may include delivering energy to the stomach using a first implantable device and delivering energy to a vagal nerve using a second implantable device (see, e.g., FIG. 1). Where multiple implantable devices are used, at least one of the implantable devices may be configured to detect energy delivered by another implantable device. For example, a circuit may be able to detect delivery of energy as transmitted by the body or to detect response of the body to the delivered energy. Where multiple implantable devices are used, at least one of the implantable devices may be configured to communicate with another implantable device.

As discussed herein, a therapeutic effect may be gain without any substantial contraction of stomach muscle. However, an exemplary method may include delivery of a pulse train sufficient to cause contraction of stomach muscle. Delivery of energy to a vagal nerve may aim to achieve any of a variety of results including blocking, activation, conditioning, etc.

Various exemplary methods include calling for sensing of nerve activity, calling for sensing of stomach muscle activity, and/or calling for sensing of cardiac activity.

With respect to electrode configurations, an exemplary method may include calling for delivery of energy to the stomach and calling for delivery of energy to a vagal nerve using at least one common electrode. Such a common electrode may be a case electrode of an implantable device and may be positioned intermediate an electrode for delivery of energy to a vagal nerve and an electrode for delivery of energy to the stomach. For example, the device 628 of FIG. 6 may be implanted in a location intermediate the pylorus and a portion of the anterior vagus nerve. Various exemplary methods may include calling for delivery of energy to the stomach and calling for delivery of energy to a vagal nerve using the same electrodes (e.g., optionally with different energy delivery scheme parameters).

An exemplary method optionally calls for delivery of energy to the pylorus proximate to the pyloric branch of the anterior vagus nerve (see, e.g., FIG. 4). As shown in FIG. 6, calling for delivery of energy to the stomach may include use of one or more electrodes arranged circumferentially around the stomach.

As already mentioned, various exemplary methods may be to some extent implemented through use of a computer-readable medium. For example, one or more computer-readable media may include processor executable instructions to perform at least a portion of an exemplary method (e.g., calling for delivery of energy, calling for sensing, making decisions, etc.).

An exemplary method for treating an eating or a metabolism disorder includes delivering energy to a vagal nerve to inhibit food intake, acquiring information germane to food intake, based at least in part on the information, deciding if food intake is occurring and, if so, deciding whether the food intake is scheduled and, if the food intake is not scheduled, calling for delivery of energy to stomach muscle to inhibit food intake. An exemplary method optionally includes use of a tiered therapy. For example, if a body does not respond to a first tier of therapy, then a method may call for a second tier of therapy, which may be more aggressive (e.g., additional tissue stimulation, increase in energy, frequency, etc.). A first tier may include delivery of energy to a vagal nerve and a second tier may include delivery of energy to the stomach (see, e.g., the methods 1112 and 1132 of FIG. 11). In another example, a first tier includes delivery of energy to the stomach and a second tier includes delivery of energy to a vagal nerve (see, e.g., the methods 1102 and 1122 of FIG. 11). Other combinations are possible and a multi-tier approach may include other types of energy delivery (e.g., respiratory, cardiac, other tissue).

CONCLUSION

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:

1. A method for treating an eating or metabolism disorder comprising:
   acquiring information germane to food intake;
   delivering energy to the stomach using a pulse train that comprises pulses with a pulse width less than approximately 20 ms, a duty cycle greater than approximately 20% and a pulse train duration of less than approximately 10 seconds; and
   based at least in part on the information germane to food intake, delivering energy directly to a vagal nerve in coordination with the energy delivered to the stomach.

2. The method of claim 1 wherein the pulse train duration is greater than approximately 2 seconds.

3. The method of claim 1 wherein the pulse train comprises biphasic pulses.

4. The method of claim 1 wherein the pulse train comprises multiphasic pulses wherein each phase of a multiphasic pulse comprises a phase width of less than approximately 10 ms.

5. The method of claim 1 wherein the pulse train comprises a pulse frequency of approximately 1 Hz to approximately 1000 Hz.

6. The method of claim 1 wherein the calling for delivery of energy to the stomach comprises calling for delivery of energy to the distal antrum proximate to the pylorus or pre-pyloric region of the stomach.

7. The method of claim 1 wherein the calling for delivery of energy to a vagal nerve comprises calling for delivery of energy to a sub-diaphragmatic portion of an anterior vagus nerve.

8. The method of claim 1 wherein the calling for delivery of energy to the stomach and the calling for delivery of energy to a vagal nerve occur at different times.

9. The method of claim 1 wherein the calling for delivery of energy to the stomach and the calling for delivery of energy to a vagal nerve occur approximately simultaneously.

10. The method of claim 1 wherein the calling for delivery of energy to the stomach and the calling for delivery of energy to a vagal nerve call for delivery of energy using the same electrodes.

11. The method of claim 1 wherein the calling for delivery of energy to the stomach calls for delivery of energy using one or more electrodes arranged circumferentially around the stomach.

12. The method of claim 1 wherein the calling for delivery of energy to the stomach calls for delivery of energy to the pylorus proximate to the pyloric branch of the anterior vagus nerve.

13. The method of claim 1 further comprising calling for delivery of energy to a splanchnic nerve.

14. A method for treating an eating or a metabolism disorder, the method comprising:
- delivering energy directly to a vagal nerve to inhibit food intake;
- acquiring information germane to food intake;
- based at least in part on the information, deciding if food intake is occurring and, if so, deciding whether the food intake is scheduled; and
- if the food intake is not scheduled, adjusting the energy delivered to the vagal nerve and calling for delivering energy to stomach muscle to inhibit food intake.

15. The method of claim 14 wherein the calling for delivery of energy to stomach muscle calls for delivery of energy sufficient to cause contraction of stomach muscle.

16. An implantable device comprising:
- means for delivering energy directly to a vagal nerve to inhibit food intake;
- means for acquiring information germane to food intake;
- means for deciding if food intake is occurring based at least in part on the information and, if so, deciding whether the food intake is scheduled; and
- means for adjusting the energy delivered to the vagal nerve and calling for delivering energy to stomach muscle to inhibit food intake if the food intake is not scheduled.

* * * * *